United States Patent [19]
Chan

[11] Patent Number: 5,911,862
[45] Date of Patent: Jun. 15, 1999

[54] MATERIAL FOR ESTABLISHING SOLID STATE CONTACT FOR ION SELECTIVE ELECTRODES

[75] Inventor: Andy D. C. Chan, Franklin, Mass.

[73] Assignee: Chiron Diagnostics Corporation, E. Walpole, Mass.

[21] Appl. No.: 08/929,195

[22] Filed: Sep. 8, 1997

Related U.S. Application Data

[63] Continuation of application No. 08/509,001, Jul. 28, 1995, abandoned, which is a continuation-in-part of application No. 08/121,822, Sep. 15, 1993, Pat. No. 5,804,049.

[51] Int. Cl.⁶ .................................................. G01N 27/333
[52] U.S. Cl. ...................... 204/418; 204/416; 205/787.5; 205/789.5; 427/58
[58] Field of Search .................................. 204/415, 416, 204/418, 419

[56] References Cited

U.S. PATENT DOCUMENTS

| | | | |
|---|---|---|---|
| 3,714,015 | 1/1973 | Niedrach | 204/415 |
| 4,020,830 | 5/1977 | Johnson et al. | 204/418 |
| 4,214,968 | 7/1980 | Battaglia et al. | 204/418 |
| 4,434,249 | 2/1984 | Ballestrasse et al. | 521/27 |
| 4,502,938 | 3/1985 | Covington et al. | 204/418 |
| 4,571,292 | 2/1986 | Liu et al. | 204/415 |
| 4,734,184 | 3/1988 | Burleigh et al. | 204/409 |
| 4,739,380 | 4/1988 | Lauks et al. | 357/25 |
| 4,816,130 | 3/1989 | Karakelle et al. | 204/418 |
| 4,981,570 | 1/1991 | Yamaguchi et al. | 204/418 |
| 5,078,856 | 1/1992 | Yamaguchi et al. | 204/418 |
| 5,120,422 | 6/1992 | Liu et al. | 204/416 |
| 5,183,549 | 2/1993 | Joseph et al. | 204/415 |

FOREIGN PATENT DOCUMENTS

| | | |
|---|---|---|
| 0 267 892 | 5/1988 | European Pat. Off. . |
| 0 325 562 | 7/1989 | European Pat. Off. . |
| 0 498 572A2 | 8/1992 | European Pat. Off. . |
| 0 498572 A2 | 8/1992 | European Pat. Off. . |
| 32 22 464 | 12/1982 | Germany . |
| 91/11710 | 8/1991 | WIPO . |
| WO 91/11710 | 8/1991 | WIPO . |
| 97/05478 | 2/1997 | WIPO ........................ G01N 27/333 |

OTHER PUBLICATIONS

Annaka, M. et al., "Multiple Phases of Polymer Gels", *Nature*, vol. 355, p. 430 (1992) month unavailable.

Ballestrasse et al., "Acrylic Ion–Transfer Polymers", *Journal of the Electrochemical Society*, vol. 134, No. 11, p. 2745 (1987) month unavailable.

Bouklouze, A. et al., "Barium Ion–Selective Electrode Based on a New Neurtral Carrier Complex", *Analytica Chimica. Acta*, vol. 273, p. 153 (1993) month available.

Cadogan et al., "All–Solid–State Sodium–Selective Electrode Based on a Calizaerne Ionophore . . . ", *Analytical Chemistry*, vol. 64, p. 2496 (Nov. 1, 1992).

El–Jammal, A. et al., "Use of Ethylene–Vinyl–Acetate as a New Membrane Matrix for Calcium Ion–Selective Electrode Preparation", *Talanta* vol. 38, No. 8, p. 929 (1991) month unavailable.

(List continued on next page.)

*Primary Examiner*—T. Tung
*Attorney, Agent, or Firm*—Arthur S. Morgenstern; Stanley Sacks

[57] ABSTRACT

A polymeric material which to form a stable, reproducible interface between the ionic and electronic domains of an ion selective sensor, or an ion selective field effect transistor, or the like is provided. When employed in an ion selective sensor, the polymeric material is advantageously provided over a solid internal reference electrode and an ion selective membrane is provided thereover. According to one embodiment, the polymeric material of the invention includes less than about $1.63 \times 10^{21}$ immobilized charged sites per gram (less than about 2.72 millaequivalents/gram). According to another embodiment, the polymeric material includes immobilized sites of charge opposite that of mobile ions involved in the redox couple. A preferred polymeric material comprises a copolymer of methacrylamidopropyl-trimethylammoniumchloride and methylmethacrylate. In a particularly advantageous embodiment, the ion selective membrane has little or no plasticizer.

30 Claims, 3 Drawing Sheets

OTHER PUBLICATIONS

Morf, W. et al., "Influence of Anionic Sites in Solvent Polymeric Membranes . . . ", *Analytical Letters,* vol. 22, No. 5, p. 1171 (1989) no month.

Oesch, U. et al., "Ion–Selective Membrane Electrodes for Clinical Use" *Clinical Chemistry,* vol. 32, No. 8, p. 1448 (1986) month unavailable.

Oniciu, L, et al., "Sturctural Studies on Ion Exchange Membranes Obtained by Functionalization of Polymer Foils", *Materiale Plastice,* vol. 25, No. 4, p. 177 (1988) month unavailable.

Sandifer, J., "Theory of Interfacial Potential Differences: Effects of Adsorption . . . ", *Analytical Chemistry,* vol. 60, p. 1553 (1988) month unavailable.

Tan, S. et al., "Reversible Optical Sensing Membrane for the Determination of Chloride in Serum", *Analytica Chimica. Acta,* vol. 255, p. 35 (1991) month unavailable.

Van den Vlekkert et al., "Multi–Ion Sensing System Based on Glass–Encapsulated pH–ISFETs and a Pseudo–REFET", *Sensors and Actuators,* B1, 395 (1990) month unavailable.

Ballestrasse et al, "Acrylic Ion–Transfer Polymers", Journal of the Electrochemistry Society, 134, 11(1987) month unavailable.

Cadogan et al, "All–Solid–State Sodium–Selective Electrode Based on a Calizaerne Ionophore . . . ", Analytical Chemistry, 64, 2496 (Nov. 1, 1992).

Van den Vlekkert et al, "Multi–Ion Sensing System Based on Glass–Encapsulated pH–ISFETs and a Pseudo–REFET", Sensors and Actuators, B1, 395 (1990) month unavailable.

Anal. Chim. Acta 255, 35 (1991) month unavailable.

Anal. Chim. Acta 273, 153 (1993) month unavailable.

Talanta 38, 929 (1991) month unavailable.

Clinical Chemistry 32, 1448 (1986) month unavailable.

Material Plastice 25, 177 (1988) month unavailable.

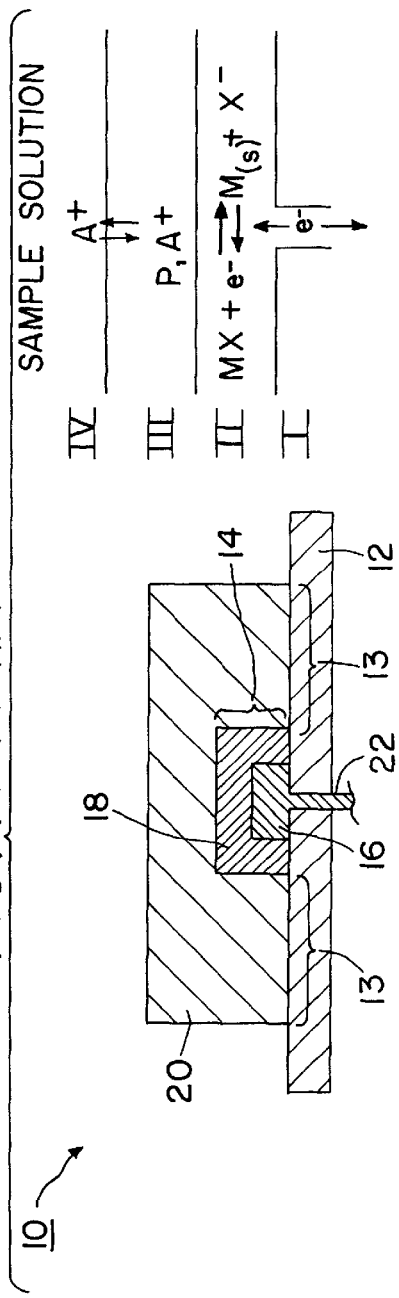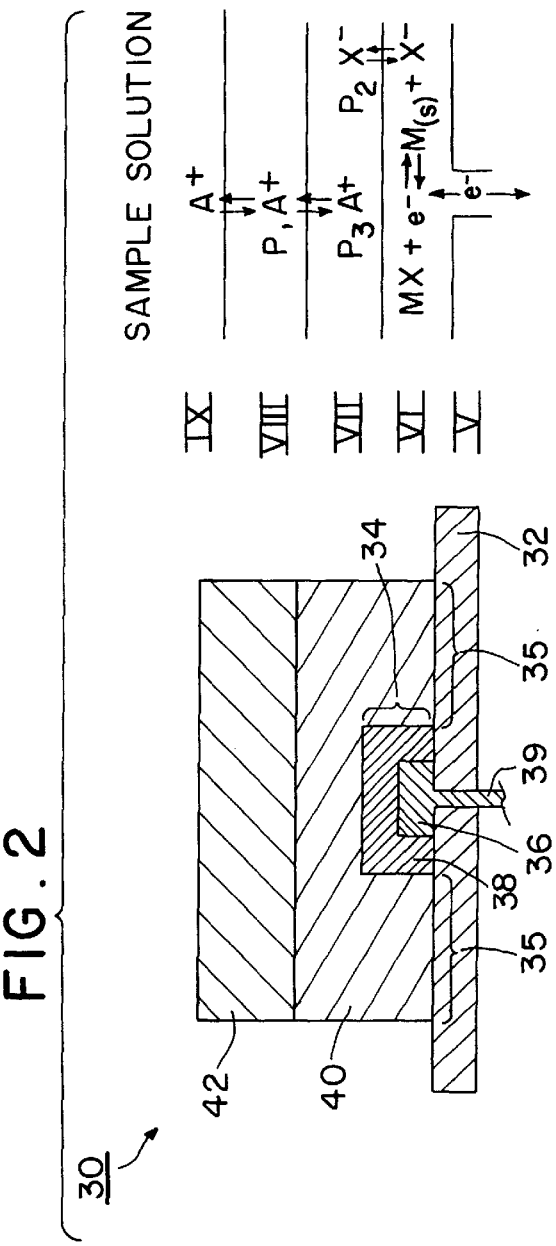

MATERIAL FOR ESTABLISHING SOLID STATE CONTACT FOR ION SELECTIVE ELECTRODES

CROSS-REFERENCE TO RELATED APPLICATION

This application is a continuation of application Ser. No. 08/509,001, filed Jul. 28, 1995, now abandoned, which is a continuation-in-part of U.S. patent application Ser. No. 08/121,822, filed Sep. 15, 1993, now U.S. Pat. No. 5,804,049.

FIELD OF THE INVENTION

The present invention relates generally to ion selective electrodes, ion selective sensors, and ion selective field effect transducers, and more specifically to a solid contact material for use in such devices membranes included therein which have a reduced amount of plasticizer.

TECHNICAL REVIEW

In many settings, for example the clinical laboratory or the analytical or industrial chemical laboratory, the need for rapid analysis of the concentration of a variety of ionic species or analytes in solution exists. Conventionally, in such analyses, an ion selective electrode is brought into contact with a test solution into which a reference electrode is also immersed. The ion selective electrode and the reference electrode are connected via a voltmeter and a potentiometric determination of the activity of a particular analyte in solution is made. The activity measurement may be correlated to the concentration of the analyte in solution using reference solutions or standard solutions of known concentration.

Typically, ion selective electrodes have been fabricated according to the following designs. One conventional design consists of an internal redox couple reference electrode, an ion-selective membrane, and an internal liquid electrolyte contacting the reference electrode and the membrane. The ion selective membrane is advantageously fabricated so as to include therein a particular molecule selectively complexing the ion to be analyzed, and the electrolyte advantageously includes a relatively high concentration of the ion to be analyzed and the anion of the redox couple, for example chloride in a silver/silver chloride reference. The potentiometric determination is based upon the principle that the electromotive force detected by the voltmeter is proportional to the logarithmic concentration of analyte in solution. Standard solutions of known analyte concentrations are typically used and a calibration curve is established in such analyses, and the concentration of analyte in the test sample is determined by comparison with the calibration curve. However, such a system requires maintenance of the electrode in an environment in which the electrode is not permitted to dry out, and is not amenable to electrode significant miniaturization, for example in the fabrication of planar electrodes.

Hydrogels, that is, neutral polymeric matrices incorporating salts, have been employed in ion selective electrodes in a manner similar to that of the above-described liquid electrolyte. However, hydrogels tend to swell unacceptably during use. Such swelling may have several detrimental effects, one of which is physical disruption, ultimately rupture, of the overlaying ion selective membrane, and another of which is unstable concentration of the analyte ion within the hydrogel as the swell value changes, resulting in imprecision and inaccuracy in analysis.

Another ion selective electrode design involves a reference redox couple, for example a silver/silver chloride electrode, covered with a conventional ion selective membrane, and is known as a "coated wire electrode". Such a design would appear to be amenable to miniaturization and to planar electrode fabrication. However, in an ion analysis system, it is important that junction potentials at material and phase interfaces of the overall voltametric determination circuit be as stable and reproducible as possible, so as to assure precision and accuracy in analysis. Instability in interface junction potential of the ion selective membrane/reference redox couple interface is observed in coated wire electrodes, at which a border between a domain of electronic conductivity and ionic conductivity exists, which border is void of chemical or electronic equilibria thereacross due to the lack of an internal contacting solution. Such a border is known in the art as a "blocked" interface.

One method of stabilizing such a junction potential is described in pending U.S. patent application Ser. No. 07/650,347, filed Feb. 4, 1991, now abandoned, assigned to the assignee of this application, and corresponding European Patent Publication No. 0498572 A2, published Aug. 12, 1992, both of which are incorporated herein by reference. Described is a redox couple reference contacted by an ion selective membrane including a fortiophore designed to complex an ionic species of the redox couple.

U.S. Pat. No. 4,434,249 describes the preparation of ion-transfer membranes and methods of preparing such membranes from acrylic monomers and, particularly, of copolymers of at least two acrylic monomers. Specifically described is a membrane composition having a monomeric component (>88 mol %) of a non-ionic hydrophobic monomeric component (3–12% mol %) of an acrylic monomer containing ionogenous groups such as methacrylamidopropyltrimethylammonium chloride (MAPTAC). The patent describes an optimum concentration level of the ionogenous monomer for transfer of ions across this bulk material, departures from which will decrease transference. No teaching is made of utilizing the material as an interface between two different conducting domains, for example, electronic and ionic domains.

European Patent Publication No. 0325562 A2, incorporated herein by reference, describes an ion selective electrode in which an ion exchange resin is incorporated between an electrochemical redox couple and an ion selective membrane, the ion exchange resin being selected so as to have ions counter to those to be analyzed chemically linked to the polymer defining the resin. The publication teaches the use of standard, commercially-available ion exchange resins, for example, Amberlite, Dowex, and Nafion, which typically have a capacity on the order of 4.3 milliequivalents per gram, that is, about $2.5 \times 10^{21}$ charged sites per gram of material. While neither aqueous swell values nor adherence characteristics of this approach are documented in the publication, ion exchange resins typically swell unacceptably in such circumstances, even to the point of dissolving, and adherence between an ion exchange resin and an inert substrate is generally thought to be poor. Indeed, adhesion between many polymeric materials incorporating charged groups and other polymeric layers or substrates must often be augmented by an intermediate, inert, mesh-like layer such as, for example, silated polyvinylchloride.

Ion selective membranes have also been used as gate materials in ion selective field effect transistors. An electronic/ionic domain boundary complication exists in that technology as well.

Therefore, it remains a challenge in the art to formulate a solid state material to serve as an interface between the electronic and ionic domains of ion selective sensors, ion selective field effect transducers, and the like, such material having a rapidly equilibrating, reproducible swell value below that at which physical disruption of any device in which it is employed occurs, which is easy to prepare and use, and which adheres well to typical substrates and to adjacent layers in devices in which it is employed.

Others have developed a reduced plasticizer ion selective membrane for use in ion selective electrode constructions. Such reduced plasticizer membranes can be made of ethylene vinyl acetate polymeric materials with or without PVC and various other materials having constructions as will be described in this application. It has now been found that such membranes have particular advantage when combined with the particularly advantageous ion sensors as are used in the present invention.

Accordingly, it is a general purpose of the present invention to provide a means and method of establishing or maintaining a more stable equilibria between electronic and ionic domains, which equilibria facilitate stable and reproducible junction potentials in electrochemical devices, using a material which is easy to prepare and use, which adheres well to typical substrates and adjacent materials in electrochemical devices in which it is employed, and which has a stable and reproducible swell value.

SUMMARY OF THE INVENTION

Objects and advantages of the present invention are achieved by providing an ion selective sensor comprising an electrically conductive material providing a reference redox couple, a polymeric material having immobilized charged sites provided on the electrically conductive material, and an ion selective membrane covering the polymeric material. Preferably, the polymeric material carries less than about $1.63 \times 10^{21}$ immobilized charge sites per gram. The ion selective electrode may additionally comprise a substrate onto which the electrically conductive reference electrode material is deposited.

It is another object of the present invention to provide an ion selective sensor comprising an electrically conductive material providing a reference redox couple, a polymeric material provided on the electrically conductive material, the polymeric material having immobilized sites of charge opposite that of mobile ions involved in the redox couple, and an ion selective membrane covering the polymeric material.

It is another object of the present invention to provide a method of providing a stable and reproducible electrical interface between a solid contact reference providing a redox couple and an ion selective membrane of an ion selective sensor or the like, comprising contacting both the solid contact reference and the ion selective membrane with a polymeric material having immobilized charged sites, the polymeric material carrying less than about $1.63 \times 10^{21}$ immobilized charged sites per gram.

It is an object of the present invention to provide a method of forming an ion selective sensor comprising the steps of providing an electrically conductive material creating a redox couple including a portion of the electrically conductive material, coating the redox couple with a polymeric material having immobilized charged sites, and covering the polymeric material with an ion selective membrane.

It is a further object of the present invention to provide an ion selective sensor which includes an ion selective membrane which has a relatively low concentration of plasticizer or substantially no plasticizer.

It is still a further object of the present invention to provide an ion selective sensor in accordance with the preceding object, wherein the membrane is relatively easy to prepare.

It is yet a further object of the present invention to provide an ion selective membrane for use in the ion selective sensors of this invention, which provides good adhesion.

It is an object of the present invention to provide a method of providing a stable and reproducible electrical interface between a solid contact reference providing a redox couple and an ion selective membrane of an ion selective sensor or the like, comprising contacting both the solid contact reference and the ion selective membrane with a polymeric material having immobilized sites of charge opposite that of mobile ions involved in the redox couple.

It is another object of the present invention to provide a method of forming an ion selective sensor comprising the steps of providing an electrically conductive material, creating a redox couple including a portion of the electrically conductive material, coating the redox couple with a polymeric material having immobilized sites of charge opposite that of mobile ions involved in the redox couple, and covering the polymeric material with an ion selective membrane.

It is another object of the present invention to provide a chemical responsive field effect transducer comprising a layer of semiconductor material having a surface, a pair of first diffusion regions of a first doping characteristic at the surface, a second diffusion region of a second doping characteristic at the surface between the pair of first diffusion regions, an electrically insulating material provided on the surface, a polymeric material having immobilized charged sites provided on the electrically conductive material, the polymeric material carrying less than about $1.63 \times 10^{21}$ immobilized charged sites per gram, the polymeric material separated from the diffusion regions by the insulating material, an ion selective membrane provided on the polymeric material, and an electrically insulating encapsulant sealing the transducer from a sample region while leaving exposed a region of the ion selective membrane for exposure to a sample.

It is still another object of the present invention to provide a method of making a chemical responsive field effect transducer comprising the steps of providing a layer of semiconductor material having a surface, doping a pair of first regions at the surface to provide a first doping characteristic therein, doping a second region of said surface between the pair of first regions so as to provide a second doping characteristic therein, covering the diffusion regions with an electrically insulating material, providing a polymeric material adjacent the electrically insulating material, the polymeric material having immobilized charged sites and carrying less than about $1.63 \times 10^{21}$ immobilized charged sites per gram, covering the polymeric material with an ion selective membrane, and encapsulating the transducer with an electrically insulating encapsulant so as to separate the transducer from a sample region while leaving exposed a region of the ion selective membrane for exposure to a sample.

One embodiment of the present invention includes an ion selective membrane which comprises an ethylene vinylacetate (EVA) polymer. The EVA polymer includes from about 30 weight percent to about 75 weight percent vinylacetate monomer, from about 0% to about 20% plasticizer by weight and at least one ion selective material. The membrane is from about 0% crystalline to about 10% crystalline.

Another embodiment of the present invention includes an ion selective membrane comprised of ethylene monomers, vinylacetate monomers and monomers of at least one additional vinyl species having a charged site or a polar group. The polymer includes from about 35 weight percent to about 55 weight percent vinyl acetate monomer and is substantially devoid of plasticizer. The membrane additionally includes at least one ion selective material. The membrane is from about 0% crystalline to about 10% crystalline.

It is a feature of the present invention that the preferred membranes for use in the ion selective sensors of this invention include little or no plasticizer and, in certain embodiments, have low crystallinity, extended lifetimes or both. Moreover, in certain embodiments, reduced plasticizer membranes may provide improved water uptake characteristics.

BRIEF DESCRIPTION OF THE DRAWINGS

The above and other features, objects and advantages of the present invention will be better understood from the following specification when read in conjunction with the accompanying drawings, in which:

FIG. 1 is a cross-sectional, schematic view of an ion selective electrode according to the prior art;

FIG. 2 is a cross-sectional, schematic view of an ion selective electrode according to one embodiment of the present invention;

DESCRIPTION OF PREFERRED EMBODIMENTS

Figure 3:
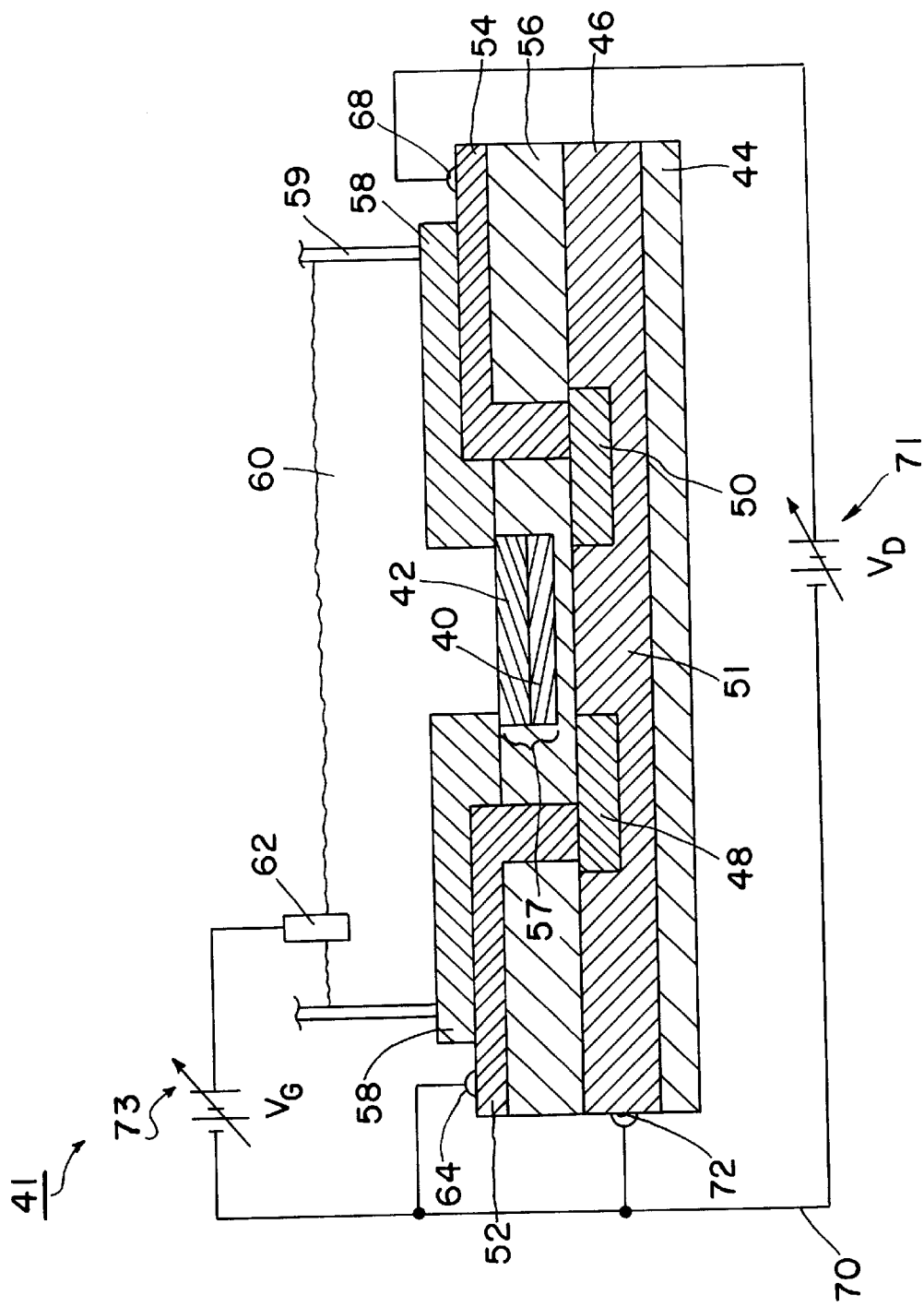
FIG. 3 is a cross-sectional, schematic view of an ion selective field effect transistor according to one embodiment of the present invention.

A prior art coated wire ion selective sensor 10 is illustrated in cross-section in FIG. 1, and includes a substantially planar non-conducting substrate 12, and redox couple 14 fabricated thereon. Redox couple 14 typically comprises a metal 16 such as silver, onto which a salt of the metal 18 such as silver chloride is electrochemically deposited. Ion selective membrane 20 is deposited thereover, typically covering redox couple 14 and contacting portions of substrate 12 in areas 13 surrounding redox couple 14 which redox couple 14 does not cover. Membrane 20 typically comprises a polymeric membrane incorporating an ion selective species which imparts ion selectivity to the membrane. Such ion selective species may take the form of, for example, a non-dissociable ion-specific ligand, i.e. an ionophore, or an electrically charged liquid ion-exchanger.

Lead 22, typically formed of a conductive material such as the metal which comprises metal 16, may pass through substrate 12 just under metal 16 to make contact therewith, as illustrated in FIG. 1, or may be deposited upon substrate 12 so as to make contact with metal 16. According to the latter arrangement (not illustrated), lead 22 would typically be covered by an electrically insulating material at portions which would otherwise make contact with membrane 20. Both of these arrangements are well-known in the art.

The scheme at the right of FIG. 1 represents, approximately, the chemical and electrochemical equilibria associated with ion selective electrode 10. In the scheme of FIG. 1, level I represents electronic contact between reference redox couple 14 and lead 22 of circuitry defining analytical apparatus. Level II represents the electrochemical equilibrium associated with typical reference redox couples, for example, one in which M represents a metal such as silver and MX represents the salt of the metal, X being an ion such as chloride. In level III, $P_1A^+$ represents the association between the material of ion selective membrane 20, $P_1$, typically polymeric material including an ionophore, and analyte species analyte $A^+$, a cation according to this exemplary scheme. Level IV represents the analyte medium, typically an aqueous solution containing analyte $A^+$. From the scheme of FIG. 1, it can be seen that equilibria exist between levels I and II in the form of electron transport and between levels III and IV in the form of ionic transport, but that no equilibrium exists between levels II and III, representing the interface of reference redox couple 14 and ion selective membrane 20, and resulting in a "blocked" interface. As described above, such a "blocked" junction potential is typically unstable and irreproducible, resulting in imprecision and inaccuracy in electrochemical analysis.

An ion selective sensor 30 in accordance with one embodiment of the present invention is schematically illustrated in cross-section in FIG. 2, typically fabricated atop substantially planar non-conducting substrate 32, and comprises reference redox couple 34, polymeric material 40 in contact therewith, and ion selective membrane 42 in contact with polymeric material 40.

Substrate 32 may comprise any electrically insulating material such as glass, ceramic, silicon wafer, plastic, polymer resin or the like, the particular substrate material or its configuration not being critical to the present invention.

Redox couple 34 is typically deposited atop a portion of substrate 32 and may comprise any standard redox reference couple, for example a metal 36 and a salt of the metal 38. In a preferred embodiment, redox couple 34 comprises a layer of silver 36 with a layer of silver chloride 38 in contact therewith, typically created or deposited thereover. Silver chloride layer 38 may be made according to any known method, for example by printing using standard microfabrication techniques, or by plating from solution, for example from a concentrated solution of potassium chloride or sodium chloride.

Lead 39 provides electrical contact for couple 34, and may pass through substrate 32 (as illustrated) or may be deposited upon substrate 32 (not shown). Lead 39 may be made from any conductive material such as silver, copper, nickel, gold, platinum, zinc, etc., and typically comprises silver, platinum, or gold according to preferred embodiments of the present invention.

Contacting redox couple 34, and completely covering redox couple 34 and extending onto portions 35 of substrate 32 according to preferred embodiments of the present invention is polymeric material 40. Material 40 may be provided upon redox couple 34 and substrate 32 according to any of the well-known methods for depositing polymeric materials onto other materials, for example by casting from solution as a dissolved polymer or copolymer, polymerizing or copolymerizing the material directly upon the redox couple and substrate, or fabricating a sheet of material 40 and pressing it onto redox couple 34 and substrate 32. According to preferred embodiments of the present invention, polymeric material 40 is cast from solution, either by spin-casting or drop-casting onto redox couple 34 and substrate 32. The solution employed may be any solution in which polymeric material 40 is soluble, typically an organic solvent.

Polymeric material 40 may comprise any material having sufficient molecular weight to form a film or coating on redox couple 34 and substrate 32, yet have a molecular weight low enough to be non-crystalline in character, typically in the range of 2,000 to 250,000 Daltons, more typically in the range of 5,000 to 150,000 Daltons.

Preferably, polymeric material 40, when contacted with water, relatively quickly and reproducibly equilibrates to a stable swell value. Material 40 should swell so as to comprise a weight not more than 5 times its dry weight when contacted with water, preferably from about 1.5 to about 3 times its dry weight, and more preferably does not swell to more than about 2 times its dry weight when contacted with water. As noted above, rapid and stable equilibration of the swell value of a material involved in electronic or ionic conductivity of an ion selective sensor or other electrochemical device results in rapid and stable equilibration of the overall electrode in terms of precision and accuracy in readout.

According to one embodiment of the present invention, polymeric material 40 comprises less than about $1.63 \times 10^{21}$ immobilized charged sites per gram (corresponding to less than about 2.72 milliequivalents/gram (meq/g)). As used herein, charged sites per gram and meq/g refer to dry weight of polymeric material 40. Preferably, material 40 comprises from about $5.5 \times 10^{19}$ to about $1.4 \times 10^{21}$ immobilized charged sites per gram (from about 0.09 to about 2.26 meq/g), more preferably from about $4.1 \times 10^{20}$ to about $1.1 \times 10^{21}$ immobilized charged sites per gram (from about 0.68 to about 1.81 meq/g), and most preferably from about $5.5 \times 10^{20}$ to about $8.2 \times 10^{20}$ immobilized charged sites per gram (from about 0.91 to about 1.36 meq/g). Employment of material 40 including these preferred ranges of the number of immobilized charged sites/gram advantageously affects the overall performance of ion selective sensor 30, especially in terms of swell, adherence, longevity, and precision and accuracy.

According to another embodiment of the present invention, polymeric material 40 has immobilized sites of charge opposite that of mobile ions involved in redox couple 34. That is, if a typical silver/silver chloride redox couple is employed as a reference 34, polymeric material 40 advantageously includes immobilized positively charged sites, counter to the chloride ions involved in the redox couple. Such a choice of charged polymeric material results in stable equilibrium between reference redox couple 34 and polymeric material 40, as will be further described below.

Polymeric material 40 may comprise the polymerization or copolymerization product of at least one monomer carrying at least one charged site, and at least one inert monomer. Preferably, material 40 comprises the polymerization product of anionic, cationic, or zwitterionic species, and typically at least one other non-ionic species. A nonlimiting exemplary list of charged sites which may be associated with species polymerized to form material 40 includes sulfonate, carboxylate, phosphonate, ammonium groups, quaternary ammonium groups, phosphonium groups, quaternary phosphonium groups, etc. A wide range of counter ions to balance these charged groups may be employed, and ions to be analyzed by the electrode of the invention and/or ions participating in the reference redox couple may be advantageously selected as counter ions.

An exemplary list of polymers suitable for use as material 40 includes polystyrene having fixed charged sites, perfluorinated ionomers, sulfonated styrene-divinyl benzene resins, divinyl naphthalene acid polymers, vinyl pyridinium salts, quaternized vinyl benzyl halides, acrylate polymers such as those described in copending, commonly-owned U.S. patent application Ser. No. 08/045,847, filed Apr. 9, 1993, now U.S. Pat. No. 5,387,329, and incorporated herein by reference, nitrile-containing polymers, amide-containing polymers, and the like.

A particularly preferred class of monomers suitable for polymerization or copolymerization to form polymeric material 40 of the present invention is described in U.S. Pat. No. 4,434,249, and an article entitled "Acrylic Ion-Transfer Polymers", issued Feb. 28, 1984, by C. L. Ballestrasse and T. R. Beck, Journal of the Electrochemical Society, 134, 11, 2745–2749 (1987), both of which are incorporated herein by reference.

According to one preferred embodiment, polymeric material 40 comprises the copolymerization product of at least one charged acrylic monomer and at least one neutral acrylic monomer. Preferably, the charged acrylic monomer or monomers employed has the formula:

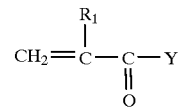

where $R_1$ is selected from the group consisting of hydrogen, hydrocarbons groups, and alcohol groups, and Y has the formula:

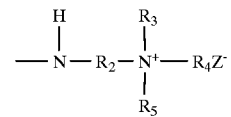

where $R_2$ is selected from the group consisting of straight or branched saturated hydrocarbon chains, straight or branched unsaturated hydrocarbon chains and straight or branched saturated or unsaturated hydrocarbon chains having hydroxy finctionalities, $R_3$, $R_4$, and $R_5$ are each selected from the group consisting of hydrogen, hydrocarbon groups, and alcohol groups, and can be the same or different, and $Z^-$ is selected from the group consisting of halides, acetate, and methylsulfate ion.

More preferably, $R_1$ is selected from the group consisting of H and $CH_3$, $R_2$ is selected from the group consisting of straight and branched saturated hydrocarbon chains, $R_3$, $R_4$, and $R_5$ are each selected from the group consisting of H and $CH_3$ and can be the same or different, and $Z^-$ is a halide. According to a particularly preferred embodiment, $R_1$, $R_3$, $R_4$ and $R_5$ each comprise $CH_3$, $R_2$ is $(CH_2)_3$, and $Z^-$ is chloride.

The neutral acrylic monomer or monomers employed, according to this embodiment, may comprise at least one component of the formula $CH_2=C(R_1)(COOR_2)$, where $R_1$ and $R_2$ are each selected from the group consisting of hydrogen, hydrocarbons, and alcohols, and can be the same or different. Preferably, $R_1$ is selected from the group consisting of hydrogen and lower alkyl groups, and $R_2$ is selected from the group consisting of linear, branched and cyclic hydrocarbons and alcohols of from 1 to 20 carbon atoms. According to the above description, hydrocarbon groups such as hydrogen, alkyl, alkenyl, alkynyl, cycloalkyl, aryl, alkaryl, aralkyl, and the like may be selected.

As used herein, the terms "hydrocarbon", "alkyl", "cycloalkyl" and similar hydrocarbon terminology is meant to include alcohols and hydrogen, although specific reference to the inclusion of hydrogen and/or alcohols is frequently made herein. Examples of such groups are methyl, propenyl, ethynyl, cyclohexyl, phenyl, tolyl, benzyl, hydroxyethyl and the like.

Copolymerization of material 40 may be effected by conventional means including anionic, cationic, or free-radical polymerization initiators.

In a particularly preferred embodiment, polymeric material 40 comprises a copolymer of methacrylamidopropyltrimethylammoniumchloride (MAPTAC) and methylmethacrylate (MMA). A random copolymer may be employed, for example made from the polymerization reaction of a mixture of these monomers in a predetermined ratio, or a block copolymer comprising blocks of from about 1 to 500 monomer units of each of the above-noted monomers may be fabricated. A block copolymer may be a random mixture of blocks of a variety of molecular weights, or may be a mixture of blocks of relatively narrow molecular weights, depending upon the application. Preferably, a mixture of MAPTAC and MMA monomers are polymerized in solution.

According to one of the embodiments of the invention described above, the ratio of relative amounts of MAPTAC and MMA monomers are selected so as to provide the above-described preferred ranges of charged sites/gram (meq/g). To formulate a polymeric material carrying less than about $1.63 \times 10^{21}$ immobilized charged sites per gram, a mixture would be polymerized comprising a weight ratio of MAPTAC to MMA of less than about 60/40. To formulate a polymeric material including from about $5.5 \times 10^{19}$ to $1.4 \times 10^{21}$ immobilized charged sites per gram, a MAPTAC/MMA weight ratio of from about 2/98 to about 50/50 would be copolymerized. To formulate a polymeric material including from about $4.1 \times 10^{20}$ to about $1.1 \times 10^{21}$ immobilized charged sites per gram, a MAPTAC/MMA weight ratio of from about 15/85 to about 40/60 would be employed. To formulate a polymeric material including from about $5.5 \times 10^{20}$ to about $8.2 \times 10^{20}$ immobilized charged sites per gram, a MAPTAC/MMA weight ratio of from about 20/80 to about 30/70 would be employed.

According to embodiments hereinabove described, polymeric material 40 may include immobilized positively charged sites, negatively-charged sites, or both positively and negatively charged sites. According to embodiments in which only negatively charged or positively-charged immobilized sites exist in polymeric material 40, addition of salts to material 40 may be particularly advantageous and is within the scope of the present invention. As noted above, the counterions of the immobilized charged sites associated with material 40 may be advantageously selected so as to be the same as either analyte ions in a solution or ions involved in reference redox couple 34. Salts selected for addition to polymeric material 40 may also be advantageously selected so as to include analyte ions and/or ions involved in reference redox couple 34. For example, when a silver/silver chloride redox couple 34 is employed, ion selective membrane is selective for a particular cation, and polymeric material 40 includes immobilized positively charged sites, a salt including the cation to be analyzed and chloride may advantageously be added to polymeric material 40.

Addition of such salts to polymeric material 40 typically advantageously affects the transference characteristic of material 40. The principle transference is described in U.S. Pat. No. 4,434,249, referenced above. It is advantageous according to the present invention to fabricate ion selective sensor 30 to have an overall transference approaching an ideal value of 1.0 for the ion to be sensed, while having a transference approaching an ideal value of zero for ions of charged opposite that of the ion to be sensed. However, within polymeric material 40 itself, it is desirable that transference numbers for both cationic and anionic species be greater than zero, preferably between about 0.1 and about 1.0.

Addition of salts to polymeric material 40 may be carried out according to several methods. According to one method, polymeric material 40 may be cast as a free-standing polymer, cut to size, and soaked in an aqueous solution comprising the salt to be added. Typically, such an aqueous solution has a concentration of about 0.1–0.2M. Alternatively, material 40 may be polymerized or copolymerized in the presence of such salts, or may be drop cast or spin cast from a solution including the selected salt during the fabrication of ion sensitive sensor 30 or ion selective field effect transistors 40 or 80, described below. According to another method, salts may be screen-printed onto redox couple 34 prior to application of polymeric material 40.

According to this embodiment, a particular salt is added preferably such that the cationic and anionic transference numbers of polymeric material 40 are both within about two orders of magnitude. More preferably, a particular salt is added such that the ratio of cationic to anionic or anionic to cationic transference is not more than about 6.0, still more preferably not more than about 2.6, and most preferably not more than about 1.9. According to preferred embodiments, polymeric material 40 is selected such that such salts may be added without affecting the specificity of cationic or anionic transport within the material.

Contacting, and completely covering polymeric material 40 according to preferred embodiments of the present invention is ion selective membrane 42. In certain embodiments of the present invention, selection may be made from any of a wide variety of known materials incorporating a variety of known ionophores or ion exchangers to impart ion selectivity to the membrane 42. Ion selective membrane 42 may be a commercially-available or pre-fabricated membrane cut to size and placed atop polymeric material 40, may be fabricated and dissolved in a suitable solvent and cast onto polymeric material 40, or may be formulated and polymerized in solution atop polymeric material 40. Additionally, it is within the scope of the present invention to use other ion selective membranes such as ion selective glasses or the like as ion selective membrane 42.

A non-limiting exemplary list of materials suitable for formation of ion selective membrane 42 includes polyvinylchloride, polystyrene, polyacrylate, polycarbonates, silicone rubber, polyesters, polyamides, vinylidene chloride, acrylonitrile, polyurethanes, polyvinylidene chloride, polyvinylidene chloride copolymerized with polyvinylchloride, polyvinyl butyryl, polyvinyl formal, polyvinyl acetate, polyvinyl alcohol, cellulose esters, and copolymers of the above materials, as well as glasses. In some embodiments, plasticizers may be used in the preparation of a membrane comprising ion selective membrane 42, such as o-nitrophenyl-octyl ether, dimethylphthalate, dioctylphenyl-phosphonate, dibutylphthalate, hexamethylphosphoramide, dibutyladipate, dioctylphthalate, diundecylphthalate, dioctyladipate, dioctyl sebacate, and other conventional plasticizers.

However, a particularly advantageous embodiment of the present invention includes ion selective membrane 42 having low crystallinity.

"Low crystallinity" is herein meant to refer to crystallinity from about 0% to about 10%, more preferably from about 0% to about 5% and most preferably from about 0% to about 3%. Crystallinity as used herein corresponds to polymer crystallinity as measured using x-ray powder diffraction such as disclosed in *Makrmol. Chemie* 50, 98 (1961) and *J. Appl. Polym. Sci.* 14, 173 (1970). As known to those skilled in the art, there is generally a correlation between the crystallinity of a polymeric material and the stiffness of the polymeric material. In certain preferred membrane embodiments of the present invention, the stiffness of the membrane has particularly advantageous values when the crystallinity of the membrane is at most about 10%.

According to certain preferred embodiments, membrane 42 may have any stiffness so long as membrane 42 has low crystallinity. For these certain preferred embodiments, membrane 42 should have a stiffness at least as great as that of a membrane comprised of 33% PVC and 66% plasticizer (NPOE or DOA), and membrane 42 should have a G-modulus of from about 0.1 MegaPascal to about 2.0 MegaPascals, more preferably from about 0.3 MegaPascals to about 1.0 MegaPascals, and most preferably about 0.6 MegaPascals as measured using the DIN 53 455 method as disclosed in *Kunststoffe* 57, 321 (1967).

When membrane 42 has low crystallinity, membrane 42 is typically sensitive to ions at concentration levels as disclosed in *Anal. Sci.* 4, 547 (1988); *Anal. Chim. Acta* 255, 35 (1991); *J. Chem. Soc. Far. I* 82 1179 (1986); *Clinical Chemistry* 32, 1448 (1986); or *SPIE* 1510, 118 (1991). For example, membrane 42 may be sensitive to concentration levels of at least about: $10^{-5.8}$M for $NH_4^+$; $10^{-7.4}$M for $Ca^{2+}$; $10^{-5.3}$M for $Li^+$; $10^{-12}$M for $H^+$; $10^{-5}$M for $Mg^{2+}$ and $10^{-5.5}$M for $Na^+$. Although particular ion selectivities have been disclosed herein, according to certain preferred embodiments, membrane 42 may have any ion selectivity so long as membrane 42 has low crystallinity.

Conventionally, the ion selectivity of membrane 42 is measured by two methods. In the separate solution method, a sensor is placed in many different solutions sequentially, and the potential in each solution is measured. Each solution contains only one type of ion and counter ion. The Nicolsky equation (given below) is then applied to the measured potentials of the known concentrations to calculate the selectivity coefficients. The slope is assumed to be constant. In the method of mixed solutions, both ions of interest and interfering ions are present. The concentration of one of these ions is varied while the other is held constant. The response is fit to the Nicolsky equation to give the selectivity coefficient. The Nicolsky equation is given by:

$$E=E_c+(RT/z_iF)ln([i]+k_{ij}[j]^{zi/zj}),$$

where $E_C$ is a constant, R is the gas constant, T is temperature in units of Kelvin, i is the ion of interest, j is the interfering ion, $z_i$ is the charge of the ion of interest, $z_j$ is the charge on the interfering ion, $k_{ij}$ is the selectivity coefficient, F is the Faraday constant, and $(RT/z_iF)$ is the slope of the membrane in units of millivolts (mV) per natural log of analyte concentration.

For some preferred embodiments, while the slope of membrane 42 may have any value so long as membrane 42 has low crystallinity, membrane 42 preferably has a slope of at least about $45/z_i$mV per decade of analyte concentration, more preferably at least about $50/Z_i$mV per decade of analyte concentration and most preferably at least about $55/z_i$mV per decade of analyte concentration.

For certain preferred embodiments of the present invention, membrane 42 preferably has a thickness from about 10 microns to about 100 microns. Although certain dimensions of membrane 42 have been described herein, it is to be understood that, according to these preferred embodiments, membrane 42 may have any shape so long as it has low crystallinity.

For some preferred embodiments, the electrical resistivity of membrane 42 may be any so long as membrane 42 has low crystallinity. For these embodiments, membranes having a thickness of about 100 micrometers and an area of about 0.32 cm$^2$, typically have an electrical resistivity from about $10^4$ Ohms to about $5 \times 10^8$ Ohms, more preferably from about $10^4$ Ohms to about $2 \times 10^7$ Ohms.

For certain preferred embodiments, membrane 42 may have any lifetime so long as it has low crystallinity. For these preferred embodiments, membrane 42 preferably has a lifetime of at least 10 days with a slope of at least 85% of the theoretical value (based on the Nicolsky equation), more preferably at least 15 days with a slope of at least 85% of the theoretical value, and most preferably at least 20 days with a slope of at least 85% of the theoretical value as measured by an accelerated aging test. The accelerated aging test includes storing the material of which the membrane is comprised under pressure in water at 115° C., preparing a membrane from the material at least every two days, and testing the slope of the membrane at room temperature.

According to certain preferred embodiments of the present invention, membrane 42 comprises an EVA copolymer and at least one ion selective material. For some of these embodiments, membrane 42 may also include a plasticizer, PVC, a salt or a combination thereof. It is to be appreciated, for certain preferred embodiments, membrane 42 may include various combinations of these or other materials appropriate for use in ion selective membranes so long as membrane 42 has low crystallinity.

By "copolymer" it is herein meant to refer to a polymerization product containing more than one monomer unit. For example, the monomer units of copolymers may be arranged such that the copolymers are selected from an illustrative and nonlimiting list which includes alternating copolymers, random copolymers, block copolymers and graft copolymers. In addition, copolymers according to the present invention may be arranged such that the copolymers include, but are not limited to, linear copolymers, branched copolymers (including star copolymers, comb copolymers, ladder copolymers and semiladder copolymers) and network copolymers. While certain types of copolymers have been disclosed herein, these lists are not limiting and, for certain preferred embodiments, any copolymer may be used according to the present invention so long as membrane 42 has low crystallinity.

According to certain preferred embodiments of the present invention, membrane 42 may include a normal EVA copolymer, a modified EVA copolymer, a functionalized EVA copolymer or a modified, functionalized EVA copolymer. Preferably, membrane 42 includes a normal EVA copolymer, a modified EVA copolymer or a functionalized EVA copolymer. More preferably, membrane 42 includes a normal EVA copolymer. By "normal EVA copolymer" it is herein meant to refer to an EVA copolymer which has substantially all carbon atoms in its backbone and is comprised of substantially all ethylene and vinyl acetate monomer units. "Modified EVA copolymers" herein denote EVA copolymers which include noncarbon atoms in their backbone structures such as, for example, O, S, N atoms. A "functionalized EVA copolymer" herein refers to an EVA copolymer which includes functional groups other than those of ethylene and vinyl acetate. A "modified, functionalized EVA copolymer" herein refers to an EVA copolymer which is both a modified EVA copolymer and a functionalized EVA copolymer as defined herein. Although certain types of EVA copolymers have been disclosed herein it is to be appreciated that, according to such preferred embodiments, any EVA copolymer may be used according to the present invention so long as membrane 42 has low crystallinity.

The dielectric constant of EVA usually increases as the weight percent of vinyl acetate in the EVA increases as disclosed in *Vysokomol. Soyed.* A15, 1382 (1972) and *Kunststoffe* 57, 321 (1967). For certain preferred embodiments, the dielectric constant of membrane 42, which comprises normal EVA, is preferably from about 2.8 to about 4.5, more preferably from about 3 to about 4.5 and most preferably from about 3.3 to about 4.5. For preferred embodiments of the present invention which include modified EVA and/or functionalized EVA, the dielectric constant of membrane 42 may be as high as about 30 or as low as about 2.8. However, it is to be appreciated that, for such preferred embodiments, the dielectric constant of membrane 42 may have any value so long as membrane 42 has low crystallinity.

The molecular weight of EVA copolymers appropriate for use according certain preferred embodiments of the present invention is preferably from about 40,000 Daltons to about 500,000 Daltons, more preferably from about 100,000 Daltons to about 400,000 Daltons and most preferably about 250,000 Daltons as measured using the methods disclosed in *Br. J. Polym.* 1, 225 (1969). However, it is to be appreciated that EVA copolymers having other molecular weights may also be used for these preferred embodiments so long as membrane 42 has low crystallinity.

For some preferred embodiments of the present invention, EVA copolymers may have any second order transition temperature so long as membrane 42 has low crystallinity. For such embodiments, EVA copolymers preferably have a second order transition temperature of from about −15° C. to about −45° C., more preferably from about −15° C. to about −35° C. and most preferably from about −20° C. to about −30° C. as measured according to DIN 53 513 or as disclosed in Kautschuk u. Gummi Kunststoffe 22, 116 (1969).

For certain preferred embodiments of membrane 42 which include a plasticizer, EVA copolymers preferably include from about 30 weight percent to about 75 weight percent vinyl acetate monomers, more preferably from about 40 weight percent to about 50 weight percent vinyl acetate monomers, and most preferably about 45 weight percent vinyl acetate monomers. However, these ranges should not be construed as limiting for these embodiments. For such preferred embodiments, the weight percent of vinyl acetate for EVA used in membrane 42 for such embodiments may be any so long as membrane 42 has low crystallinity.

According to certain preferred embodiments of the present invention in which membrane 42 includes about 0% plasticizer by weight (i.e., membrane 42 is "substantially devoid of plasticizer"), EVA copolymers should include a weight percentage of vinyl acetate from about 30 percent to about 55 percent, more preferably from about 40 percent to about 50 percent vinyl acetate monomer, and most preferably from about 45 percent vinyl acetate monomer. However, it is to be appreciated that EVA copolymers appropriate for use in these preferred embodiments may comprise any mole percentage of vinyl acetate so long as membrane 42 has low crystallinity.

It should be noted that, for some preferred embodiments, having a reduced amount of plasticizer in membrane 42 increases the adhesive properties thereof relative to most known membranes used in ion selective electrodes. For some of these embodiments, the increased adhesion of membrane 42 may be advantageous.

EVA copolymers according to certain preferred membrane embodiments of the present invention may be synthesized using techniques such as disclosed in *Br. Polym. J.* 1, 225 (1969), *Kautschuk u. Gummi Kumstoffe* 2, 116 (1969), U.S. Pat. No. 3,325,460 and German Patent No. 1,126,613. These methods include, for example, high pressure radical reaction of vinyl acetate and ethylene (at pressures from about 1500 to about 2000 atmospheres), moderate pressure radical polymerization of vinyl acetate and ethylene (at pressures from about 100 to about 500 atmospheres) or emulsion polymerization. High pressure radical polymerization typically produces EVA having up to about 40% vinyl acetate by weight. Medium pressure polymerization usually results in EVA which has from about 30% to about 100% vinyl acetate produce EVA having an amount of vinyl produce EVA having an amount of vinyl acetate which covers the whole range, but the product can be highly branched or even cross-linked. For these preferred embodiments, medium pressure polymerization should be used to synthesize EVA. Other methods of synthesizing EVA are known to those skilled in the art and are intended to be within the scope of the present invention. Such techniques are limited only in that, for preferred embodiments in which the resulting EVA is incorporated into membrane 42, membrane 42 has low crystallinity.

Methods of synthesizing modified and/or functionalized EVA copolymers appropriate for use in some preferred membrane embodiments of the present invention are known to those skilled in the art and are intended to be within the scope of the present invention. For example, incorporation of non-vinyl acetate, vinyl monomers and nonethylene monomers can be accomplished by forming copolymers according to standard methods. Carbon monoxide (CO) can be polymerized with ethylene and vinyl acetate such as disclosed in *Vysokomol. Soyed.* A11, 2585 (1969). Using these methods, copolymers including ethylene, vinyl acetate and carbon monoxide with up to 70 mole percent carbon monoxide can be produced without substantially changing the crystallinity or elasticity of the material.

*J. Polym. Sci.* A11, 9, 3083 (1971) discloses methods of polymerizing a variety of compounds with ethylene and vinyl acetate such as, for example, vinyl chloride, vinyl fluoride, propylene and hexene-1. For certain preferred membrane embodiments, any of these methods and copolymers may be used according to the present invention so long as membrane 42 has low crystallinity. However, it should be noted that the crystallinity of the copolymer depends upon the monomer polymerized with ethylene and vinyl acetate. Therefore, when vinyl chloride and vinyl fluoride are incorporated into the copolymer, up to about 50 mole percent of the additional monomer may be included in the copolymer for some preferred embodiments. For certain preferred membrane embodiments, about 31 mole percent of propylene may be used, and the amount of hexene-1 used may be based on the fact that hexene-1 has substantially the same crystallinity as vinyl acetate. It should be further noted that, in some preferred embodiments, incorporating these monomers into the copolymer may change the dielectric constant of the overall polymer.

*Vysokomol. Soyed.* A11, 2585 (1969) discloses compounds that can be copolymerized with ethylene to form copolymers. These compounds include vinylene carbonate, maleic anhydride and organic esters of phosphinic acid. Typically, the monomers which are polymerized with ethylene and vinyl acetate are capable of resulting in a copolymer with a lower crystallinity than EVA. However, it should be noted that not all these additives cause a substantial change to the crystallinity of the copolymer. Accordingly, for those monomers which do not assist in decreasing the crystallinity of the overall membrane material, they are typically present in amounts of less than about 5% of the overall material by weight for certain preferred membrane embodiments. However, it is to be appreciated that, for these preferred membrane embodiments, the amount of the monomer polymerized with ethylene and vinyl acetate is limited only in that, when membrane 42 comprises the resulting copolymer, membrane 42 has low crystallinity for such preferred embodiments.

Other copolymers are known to those skilled in the art and include monomer units of, for example, 4-ethylidene-2-nobornene, 5-ethylidene-2-nobornene, hexaydrodimethanonaphthalene, N-methylacryalamide cyanurate, methylmethacrylate, methylene succinic acid, and ethylene oxide with S-trioxone. Many of the monomers which may be used to use copolymers with ethylene and vinyl acetate are capable of introducing heteroatoms (i.e., non-carbon atoms) into the backbone of the copolymer for such preferred membrane embodiments.

Ionomers appropriate for use in the membrane of the present invention can also be made from EVA synthetic methods using copolymerization in which charge groups are introduced as pendant side chains as described in *Kunststoffe* 57, 321 (1967). For some preferred embodiments, the copolymer preferably includes from about 0.001% to about 5% of the ionized charge group by weight, more preferably from about 0.1% to about 4% and most preferably 0.5% to about 2%. However, it is to be understood that, for such preferred membrane embodiments, the amount of the ionized charged group within copolymers which may be included in membrane 42 are limited only in that membrane 42 should have low crystallinity.

According to the present invention, membrane 42 may include EVA which has PVC grafted thereto. Methods of synthesizing such copolymers are known to those skilled in the art and include those disclosed in, for example, *Br. Polym. J.* 1, 225, (1969). For some preferred membrane embodiments, such copolymers typically include up to 50% grafted PVC by weight, more preferably less than about 10%.

EVA copolymers appropriate for use in certain preferred membrane embodiments of the present invention may also be synthesized by hydrolyzing the acetate group in vinyl acetate to yield vinyl alcohol. It should be noted that, as disclosed in *J. Polym. Sci.* A1, 3083 (1971), essentially all forms of ethylene vinyl alcohol have some crystallinity. Accordingly, according to some preferred membrane embodiments of the present invention, copolymers containing vinyl alcohol monomers preferably include less than about 20% vinyl alcohol by weight.

Ion selective materials appropriate for use according to the present invention should make membrane 42 permselective. Such materials are capable of complexing a desired ion and extracting an ion of one charge without extracting an ion of the opposite charge. These ion selective materials include, for example, nondissociable, ion-specific ligands, i.e., ionophores, or electrically charged liquid ion-exchangers. Ion selective materials are known to those skilled in the art and, in certain preferred embodiments of the present invention, are limited in their type and mole percent of membrane 42 only by the fact that membrane 42 and should have low crystallinity.

Preferably, membrane 42 comprises from about 0.05 percent to about 10 percent of ion selective material by weight, more preferably from about 1 percent to about 6 percent ion selective material by weight, most preferably from about 1 percent to about 3 percent ion selective material by weight. In certain embodiments, more than one ion selective material may be incorporated into membrane 42. In embodiments of the present invention which include more than one ion selective material, membrane 42 preferably comprises from about 0.05 percent to about 10 percent ion selective material by weight, more preferably from about 1 percent to about 6 percent by weight and most preferably from about 1 percent to about 3 percent by weight. However, it is to be understood that, for some preferred embodiments, membrane 42 may comprise any amount of ion selective material and any number of ion selective materials so long as membrane 42 has low crystallinity.

Ion selective materials according to the present invention may be any of those known to be selective towards a particular ion to be analyzed. An illustrative and nonlimiting list of such ion selective materials includes: for potassium, valinomycin, bis (benzo-15-crown-5)-4-ylmethyl)pimelate dicyclohexano-18-crown-6, dibenzo-18-crown-6, tetraphenyl borate, tetrakis (p-chlorophenyl) borate, cyclopolyethers, tetralactones macrolide actins (monactin, nonactin, dinactin, trinactin), the enniatin group (enniatin A, B), cyclohexadepsipeptides, gramicidine, nigericin, dianemycin, nystatin, monensin, esters of monensin, antamanide, alamethicin (cyclic polypetieds); for calcium, ETH1001 (as disclosed in *Anal. Chem.* 53, 1970 (1981), ETH129, A23187 (Fluka of Buchs, Switzerland), ETH5234 (Fluka of Buchs, Switzerland), bis (didecylphosphate), bis (4-octylphenylphosphate), bis (4-(1, 1, 3, 3-tetramethylbutyl)) phenylphosphate, tetracosamethylcyclododecasiloxane, N, N'-di ((11-ethoxycarbonyl) undecyl)-N,N'4, 5-tetramethyl-3, 6-dioxaoctane diamide, antibiotic A-23187 (as disclosed in *Ann. Rev. Biochem.* 45, 501 (1976)); for hydrogen, ETH1907 (Fluka of Buchs, Switzerland), ETH1778 (Fluka of Buchs, Switzerland), tridodecylamine, ETH1907, N-methyl n-octadecyl (1-methyl, 2-hydroxy, 2-phenyl) ethylamine, N-octadecyl 3-hydroxy N propylamine, N, N'bis (octadecyl ethylene amine), p-octadecyloxy-m-chlorophenylhydrazonemeso oxalonitrile; for sodium, monensin, ETH227 (Fluka of Buchs, Switzerland), ETH157 (Fluka of Buchs, Switzerland), ETH4120 (Fluka of Buchs, Switzerland), ETH2120 (Fluka of Buchs, Switzerland), ETH227, ETH157, $NAS_{11-18}$, N, N', N"-triheptyl-N,N', N"-trimethyl-4,4', 4"-propylidintris-(3-oxabutyramide), 4-octadecanoyloxymethyl-N, N, N', N'-tetracyclohexyl-1, 2-phenylenedioxydiacetamide, bis[(12-crown-4)methyl] dodecylmethylmalonate, ETH149, ETH1810, cyclopolyethers; for lithium, N, N'-diheptyl-N, N', 5, 5-(tetramethyl-3, 7-dioxononanediamide), ETH149 (Fluka of Buchs, Switzerland), ETH1644 (Fluka of Buchs, Switzerland), ETH1810 (Fluka of Buchs, Switzerland), ETH2137 (Fluka of Buchs, Switzerland), 6,6-dibenzyl-14-crown-4; 6,6-dibenzyl-1, 4, 8, 11-tetraoxa-cyclotetradecane (Fluka of Buchs, Switzerland), 6[2-(diethlphosphonoox)ethyl] 6-dodecyl-14-crown-4 (Fluka of Buchs, Switzerland), 12-chrown-4, 6, 6-dibenzyl-14 chrown-4, cyclopolyethers, dodecylmethyl 14-crown-4; for chloride, tridodecyl ammonium salt, 5, 10, 15, 20-tetraphenyl-21H, 23H-porphin manganese (111) chloride (Fluka of Buchs, Switzeraland), quaternary ammonium chloride and tributyl tin chloride; for rubidium, valinomycin, cyclopolyethers; for cesium, cyclopolyethers; for $HCO_3^-$-, trifluoroacetyl-p-alkylbenzenes; for $NH_4^+$, nonactin, monactin; for $NO_3^-$, tridodecylammonium chloride; and for $Mg^{2+}$, ETH7025 (Fluka of Buchs, Switzerland or as disclosed in *Anal. Chem.* 341, 727 (1991)), ETH117 (Fluka Buchs of Switzerland), ETH5214 (Fluka Buchs of Switzerland), ETH4030 (Fluka of Buchs, Switzerland) and ETH5214. Preferably, the ion selective materials include: for potassium, valinomycin; for calcium, ETH1001; for $NH_4^+$, nonactin; for hydrogen, tridodecylamine; for $NO_3^-$, tridodecylammonium chloride; for $Cl^-$, tridodecyl ammonium salt; and for sodium, ETH2120 (Fluka of Buchs, Switzerland). All ETH compounds are as disclosed in *Anal. Sci.* 4, 547 (1988) unless otherwise noted.

A "plasticizer" as used herein refers to a material which can be added to membrane 42 to reduce the stiffness thereof. Typically, such plasticizers comprise polymeric materials, organic solvents or oils which are generally known in the art as external plasticizers (i.e., not chemically incorporated into the backbone of the EVA copolymer). An illustrative and nonlimiting list of plasticizers appropriate for use in certain preferred membrane embodiments of the present invention includes dioctyl adipate (DOA), dioctyl phthalate, nitrophenyl octylether (NPOE), dimethyl phthalate, dioctylphenyl-phosphonate, dibutyl phthalate, hexamethyl phosphoramide, dibutyl adipate, diundecyl phthalate, and dioctyl sebacate (DOS). Other plasticizers are known to those skilled in the art and may be used according to certain preferred membrane embodiments of the present invention so long as membrane 42 has low crystallinity.

For certain preferred embodiments, a plasticizer can be selected based on the ion for which membrane 42 is selective. In such cases, the plasticizer may be selected by performing a test of ion selectivity and slope of response to the ion of interest. For example, when membrane 42 is intended to be selective for potassium, DOA and DOS are preferably used as plasticizers, and when membrane 42 is designed to be selective towards calcium, NPOE is the preferred plasticizer. Other plasticizers appropriate for use in membrane 10 when designed to be selective for certain ions are known to those skilled in the art and are meant to be within the scope of the present invention. Moreover, for certain preferred embodiments, a plasticizer need not be selected based on the ion toward which membrane 42 is selective so long as membrane 42 has low crystallinity. It is to be appreciated that the use of reduced amounts of plasticizers in ion selective membranes according to the present invention can result in ion selective membranes which have relatively long lifetimes as measured according to methods disclosed herein.

In some embodiments, it may be desirable to improve the ion transference characteristics and permselectivity of membrane 42 by adding a salt thereto. In some preferred embodiments of the present invention which include salts, the salt should have a mole percent of membrane 42 from about 10% to 80% of the mole percent of the ion selective material, more preferably from about 33% to 66% of the mole percent of the ion selective material and most preferably about 50% of the mole percent of the ion selective material. In certain embodiments, the added salt may also serve as an integral part of the ion selective material. For such embodiments, the amount of salt within membrane 42 should not exceed the amount of ion selective material included within membrane 42 as disclosed elsewhere herein. Preferably, the salt is $KB(C_6H_4X)_4$ where X is H, F or $CF_3$. For some preferred embodiments, the amount of salt included within membrane 42 is limited only in that membrane 42 should have low crystallinity.

Addition of salts to membrane 42 may be carried out by several methods. In certain embodiments, such salts may act as ion selective materials. According to one method, membrane 42 is cast as a free-standing material which is soaked in an aqueous solution comprising the salt to be added. Typically, such an aqueous solution has a salt concentration from about 1 mM to about 1M. Preferably, the polymer and the salt to be added are dissolved in a solvent. The salt can be at the desired mole percent relative to the polymer. The dissolved polymer and salt may then be cast. The materials of membrane 42 may be drop cast or spin cast from a solution including the salt. While some methods of incorporating salts into membrane 42 have been disclosed herein, other methods are known to those skilled in the art and are within the scope of the present invention.

For certain preferred membrane embodiments, ion selective membranes in accordance with the present invention may be made according to any method so long as membrane 42 has low crystallinity. In a preferred embodiment of the present invention, membrane 42 is prepared by dissolving an EVA copolymer in a first solvent. A solution containing the ion selective material(s) and a second solvent is then added to the EVA copolymer containing solution. The order of mixing of the above-mentioned solutions may be reversed in some embodiments. In addition, the EVA copolymer and ion selective material(s) may be dissolved within the same solvent. The resulting solution including the EVA copolymer and the ion selective material(s) is molded according to standard methods to form membrane 42 such as, for example, standard solvent casting methods. It is to be appreciated that while certain methods of forming a membrane according to the present invention have been disclosed herein, other methods of forming membrane 42 will be apparent to those skilled in the art and are intended to be within the scope of the present invention.

For certain preferred embodiments of the present invention, appropriate solvents are limited only to the extent that they should be capable of dissolving the EVA copolymer and other components of membrane 42 without changing the chemical structure of the EVA copolymer or other materials of which membrane 42 is comprised. Typical solvents include tetramethyleran (THF), carbon tetrachloride, chloroform, methylene chloride, p-xylene and toluene. Preferably, the solvent is THF. Other solvents having the aforementioned properties may also be used and are known to those skilled in the art.

For some preferred embodiments of the present invention which incorporate PVC, a plasticizer or other materials appropriate for use in membrane 42, these materials may first be dissolved in a solvent as described above and subsequently mixed with the EVA/ion selective material(s) solution. Alternatively, the order of mixing may be reversed. In addition, all the materials including the EVA copolymer and ion selective material(s) may be dissolved within the same solvent. The resulting solution may be molded as given above to form membrane 42, or other methods of forming such membranes which are known to those skilled in the art may be used.

A variety of components and methods for fabrication of ion selective membranes, in particular membranes, in accordance with the present invention are known in the art and may be found, for example, in International Patent Publication No. WO 91/1171 0, published Aug. 8, 1991, and U.S. Pat. Nos. 4,214,968, 3,562,129, 3,753,887, and 3,856,649, all of which are incorporated herein by reference, as well as commonly-owned pending U.S. patent application Ser. No. 07/650,347 and European Patent Publication No. 0325562 A2, both of which are referenced above.

Referring now to the scheme of FIG. 2, an approximation of the advantageous chemical equilibria associated with the ion selective sensor of the present invention is represented. Level V represents electronic flow to and from redox couple 34 through lead 39. Level VI represents the electrochemical equilibrium associated with redox couple 34 such as, for example, silver/silver chloride. Level VII illustrates the association of the ion $X^-$ of redox couple 34, for example chloride ion, with portions of polymeric material 40 represented by $P_2$, and the incorporation of an ion to be analyzed, for example, a cation represented as $A^+$, associated with portions of polymeric material 40 as represented by $P_3$. If immobilized positively-charged sites are associated with polymeric material 40, the association represented by $P_2X^-$ is enhanced when silver/silver halide is selected as redox couple 34, as well as association with any anion to be analyzed. If polymeric material 40 includes immobilized negatively-charged sites, association with any positive ion included in an electrochemical equilibrium associated with redox couple 34 and/or association with a positively charged ion to be analyzed, represented in FIG. 2 as cation $A^+$, is enhanced. If polymeric material 40 is selected so as to comprise only positively-charged or negatively-charged immobilized sites, it is preferably also selected so as to be able to incorporate to some extent ions of a charge the same as that of the immobilized sites, so that equilibrium both with anions associated with redox couple 34 and cations associated with the analyte species may exist (as described above), and this may ensue according to the preferred ranges of immobilized charged sites per gram of polymeric material 40 according to the present invention. Level VIII of the scheme of FIG. 2 represents portions of ion selective membrane 42, represented as $P_1$, associated with the ion to be analyzed, cation $A^+$ in this scheme. Level IX represents the analyte medium containing exemplary analyte $A^+$, which may comprise an aqueous or organic solution, blood or plasma, skin, or the like, a wide variety of analyte media being measurable with ion selective sensors fabricated in accordance with the present invention.

As can be seen from the scheme of FIG. 2, equilibria exist between each of the levels V–IX. Between levels V and VI, electronic transport exists, similarly to the state of the prior art represented by levels I and II of FIG. 1. Between levels VIII and IX, ionic transport exists, similarly to the state of transport between levels III and IV in the representation of the prior art in FIG. 1. However, according to the present invention, between levels VI and VII, ionic transport exists, aided by association between portions $P_2$ of polymeric material 40 and an ion associated with the equilibrium of redox couple 34 ($X^-$). Additionally, ionic transport between levels VII and VIII exists, in the form of exemplary analyte ion ($A^+$) transport between portion $P_1$ of ion selective membrane 42 (level VIII) and polymeric material 40 (level VII). The result is thus "unblocked" junction potential across ion selective sensor 30, resulting in improved precision and accuracy in analysis of ionic species.

As noted above, one problem commonly associated with fabrication of planar electrochemical devices is poor adherence between layers. Often delamination is a determining factor in the lifetime of a particular device, or in the feasibility of device production. The ion selective sensor of the present invention is commonly mounted in a sampling device comprising a sample chamber which is mounted so as to cover ion selective membrane 42 above redox couple 34, the sample chamber allowing a sample solution to contact membrane 42 above redox couple 34. An exemplary sample chamber is described in commonly-owned, copending U.S. patent application Ser. No. 08/045,847, referenced above. In such a sampling device, with reference to FIG. 2, a gasket or other apparatus generally applies pressure atop ion selective membrane 42 in the direction of substrate 32, which may alleviate some delamination problems once device fabrication is complete. However, typical microfabrication of such sensors involves fabrication of a plurality of devices on a single chip, followed by singulation (dicing) of the chip to provide a plurality of sensors, and then installation of each sensor device into an encasing sample device. Such singulation and separation may result in delamination if adherence between the various layers is not good.

It has surprisingly been found that polymeric material 40, according to preferred embodiments of the present invention, adheres well to a variety of insulating substrate materials and to a variety of ion selective membranes, such that auxiliary binding layers are not needed between polymeric material 40 and substrate 32 or between material 40 and membrane 42.

Mechanical adhesion of layers can be characterized by methods including the tape, blister, scratch/scrape, ultrasonic bath and peel tests. A simple yet effective semi-quantitative test for adherence is the tape test. In a typical procedure, a sensor fabricated in accordance with the present invention, schematically represented in FIG. 2, is fabricated on a chip along with a plurality of such electrodes. A piece of adhesive tape is pressed atop a chip including a plurality of such electrodes, typically a chip of about 2 inches by 2 inches in dimension, and the tape is removed by slowly pulling upwards at an angle approximately perpendicular to the surface of the chip. Tape is advantageously selected to have an adhesive strength such that if mechanical adhesion between the layers is good the tape will peel off without disrupting the layers, but if adhesion is poor delamination will occur. Alternatively, pieces of tape with increasing adhesive properties may be used in such a test until delamination of one layer from another layer occurs, or rupture of any layers occurs. A goal in fabrication of ion selective sensors such as those of the present invention is that, when tape of sufficient adhesive quality is used, rupture of ion selective membrane 42, and/or polymeric material 40 will occur rather than delamination of ion selective membrane 42 from polymeric material 40, or delamination of polymeric material 40 from substrate 32. Stated another way, the polymeric material 40 is selected so as to bond sufficiently to substrate 32 and to ion selective membrane 42 such that adhesion between polymeric material 40 and substrate 32 and between polymeric material 40 and ion selective membrane 42 is stronger than force needed to rupture either membrane 42 or material 40. Material selected as polymeric material 40 in accordance with the present invention surprisingly shows good adhesive properties. The result is surprising in that, as noted above, immobilized charged sites associated with polymeric material are thought to be inconsistent with good adhesion of such polymeric material to an insulating substrate or to adjacent layers in typical planar electrochemical devices.

Referring now to FIG. 3, a chemical-responsive transducer, and specifically an ion selective field effect transistor (ISFET) incorporating the polymeric material 40 of the present invention is schematically illustrated in cross-section. Such transducers, and particularly ISFETs, are described in "Ion Selective Electrodes And Analytical Chemistry" vol. 2, Freiser, H., Plenum Press, New York (1979), incorporated herein by reference, in U.S. patent application Ser. No. 07/650,347, referenced above, and in U.S. patent Ser. No. 4,502,938, incorporated herein by reference. As used herein, electrochemical transducer is meant to define a field effect device for use in the separate or simultaneous detection and/or measurement of various chemical properties including ion activity and concentration, presence and concentration of enzymes, substrates, antibodies, antigens, hormones, reducible gases, glucose, lactate, pyruvates, creatinine, urea, and the like. Such devices may be advantageously used for signal amplification and/or processing involved in the measurement of the above-noted species and others during flow-injection-analysis, flow-through cuvette apparatus suitable for the continuous or intermittent on-line monitoring of blood in the clinical or laboratory environment, and the like. Suitable devices which may be advantageously modified by incorporation of the polymeric material 40 of the present invention include any electrochemically-based transducer that employs an ion-selective material such as a membrane and in which conductivity across a boundary between an electrical and a chemical domain is advantageously stabilized.

An ISFET will be used to descriptively exemplify such a transducer, but it is to be understood that the electrochemical transducer of the present invention is not limited to a transistor embodiment. Such transistors are fabricated by replacing or augmenting a metal gate with an ion selective membrane such as membrane or glass, an electrolyte (or analyte) solution contacting the membrane, and a reference electrode contacting the electrolyte solution, the reference electrode being in electrical contact with the gate circuit of the ISFET.

Referring to FIG. 3, ISFET 41 is illustrated and comprises substantially planar electrically insulating substrate 44; semiconductor 46 which may be an n-doped or p-doped material, and comprising p-type silicon according to a preferred embodiment deposited atop substrate 44; diffusion regions including source 48 and drain 50 separately formed in semiconductor 46 having a first doping polarity and comprising, for example, n-type silicon according to a preferred embodiment; leads 52 and 54 contacting source 48 and drain 50, respectively, formed from any conductive material such as metal; insulating layer 56 coating semiconductor 46 (and source and drain 48 and 50 formed therein) at all places except where leads 52 and 54 contact source and drain 48 and 50, insulating layer 56 comprising $SiO_2$ according to a preferred embodiment; polymeric material 40 in accordance with the present invention formed atop insulating layer 56 above diffusion region, or channel 51 of semiconductor 46 between source 48 and drain 50, formed in well 57 according to one embodiment; ion selective membrane 42 formed atop polymeric material 40; and encapsulant 58 sealing portions of ISFET 41, and especially contacts 52 and 54, but leaving exposed a portion of ion selective membrane 42. Region 51 of semiconductor 46 between source 48 and drain 50 has a doping polarity that is either different from that of source 48 and drain 50 or of a different magnitude. For example, source 48 and drain 50 may comprise n-type silicon while region 51 may comprise p-type silicon. Alternately, source 48 and drain 50 may be relatively heavily doped to a particular polarity, region 51 being lightly doped to the same polarity.

Sample 60, which may or may not include an analyte or ion, is provided in contact with membrane 42, and reference electrode 62 is provided in contact with electrolyte or analyte solution 60. Illustrated in FIG. 3 is a liquid electrolyte 60 contacting membrane 42 and encapsulant 58 being contained within boundary 59, such as a beaker or the like. Contact 64 contacts lead 52, and contact 68 contacts lead 54, thus the drain circuit of ISFET 41 contains lead 52, contact 64, conductor 70, contact 68, lead 54, drain 50, region 51, source 48 and a potential source 71. The drain circuit is in electrical contact with reference electrode 62, thus electrode 62, electrolyte 60, ion selective membrane 42, polymeric material 40, and potential source 73 complete the gate circuit of ISFET 41. Contact 72, in electrical connection with conductor 70, may contact semiconductor 46 to provide a stable reference for the gate and drain circuits of ISFET 41.

Figure 4:
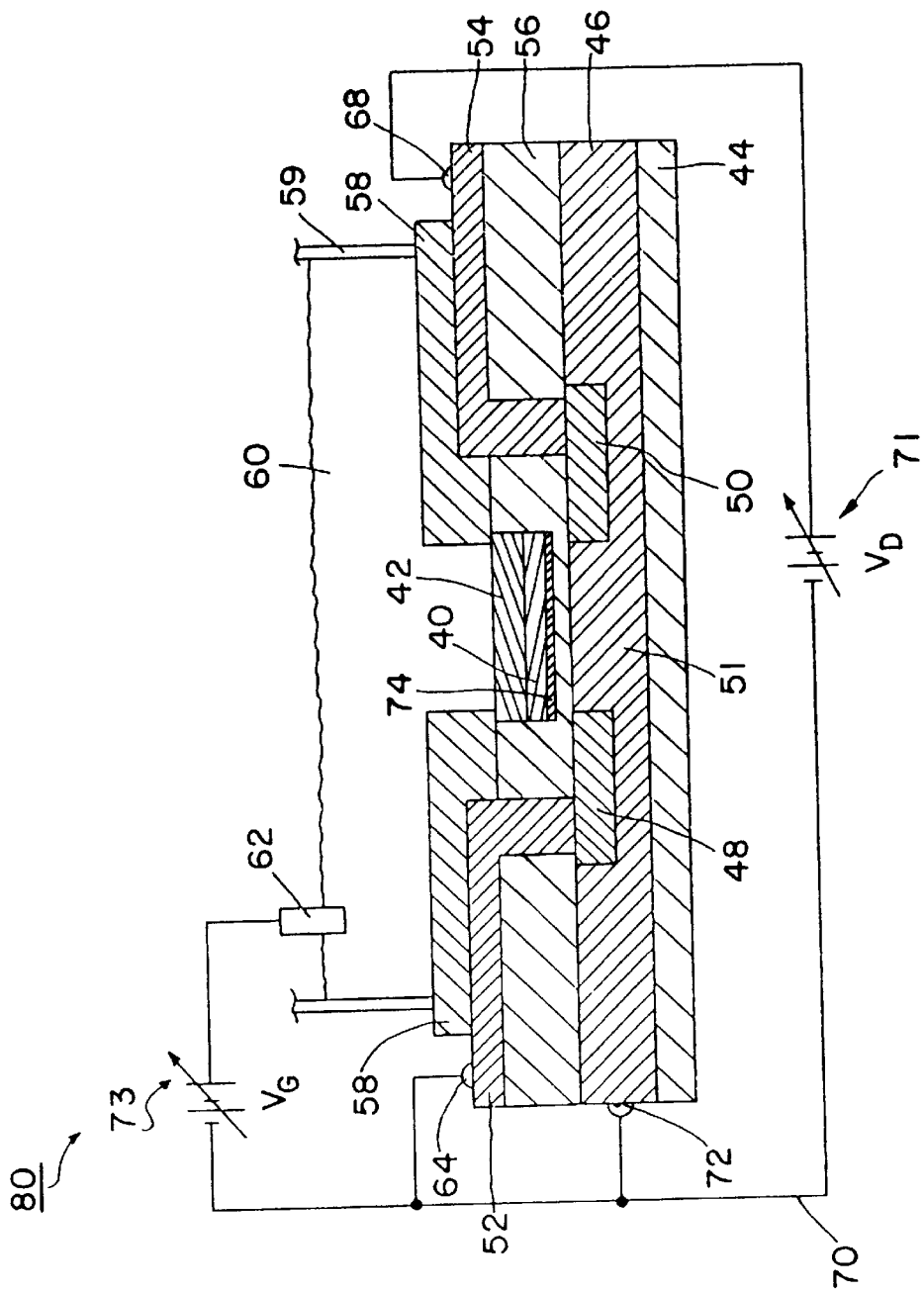
FIG. 4 is a cross-sectional, schematic view of an ion selective field effect transistor according to another embodiment of the present invention.

FIG. 4 illustrates a second embodiment of the present invention in which an ISFET incorporates polymeric material 40. Components and features common to FIGS. 3 and 4 are represented by common numerical designations. In FIG. 4, as in FIG. 3, the metal gate of a field effect transistor is replaced by ion selective membrane 42, polymeric material 40, electrolyte or analyte solution 60, and reference electrode 62. The embodiment illustrated in FIG. 4 additionally comprises ion-barrier layer 74 between polymeric material 40 and insulator 56. Layer 74 may comprise a conducting metal such as gold, silver, platinum, copper, brass, zinc, etc., or their oxides or alloys. Particularly preferred materials suitable for use as layer 74 are $Al_2O_3$, $Ta_2O_5$, and $Si_3N_4$. Exemplary materials suitable for components of ISFET 41 according to the present invention, and exemplary dimensional specifications for the components may be found in U.S. Pat. No. 4,502,938, referenced above.

The "unblocked" junction potential as described above with reference to FIG. 2, is realized according to the embodiment of the present invention defining the transducer of FIG. 3 and FIG. 4.

The dimensions of ion selective sensor 30 and ISFET 40 are not critical to the present invention. Dimensions typically found in planar electrochemical devices fabricated according to conventional thin-film or thick-film techniques are acceptable. Additionally, although substrate 32 is illustrated in FIG. 2, upon which ion selective sensor 30 is fabricated, sensor 30 may be fabricated without a substrate, in the form of the well-known "dipped" electrode. Such an embodiment will be clearly understood by referring to U.S. Pat. No. 3,714,015, and incorporated herein by reference.

In the following examples, a preliminary procedure was used to evaluate the sensors of the present invention. This preliminary procedure described is not meant to constitute a final, rigorous evaluation.

The following examples are intended to illustrate the benefits of the present invention, but do not exemplify the fall scope of the invention. For example, although the thick-film technique is exclusively exemplified, it is to be understood that the thin-film technique may be selected; although only a one-electrode device is fabricated, a device including a plurality of electrodes on a single chip could be fabricated, as well as a plurality of transducers on a single chip. Additionally, the specific shape and arrangement of the components of the electrode of the present invention may be significantly altered, such alteration being within the scope of the invention. These and other modifications and their equivalents are understood to be within the scope of the present invention.

EXAMPLE 1

In this and the following examples, ion selective sensors were fabricated by screen printing a plurality of individual electrodes on a laser scored ceramic wafer, and following; the deposition of an ion selective membrane, the wafer was singulated on the laser score lines so as to create a plurality of individual sensor chips. For the purpose of simplicity in this and the following examples, procedures will be described as if a single chip were fabricated.

An ion selective sensor base chip was fabricated on a 0.457 cm×1.143 cm electrically insulating composite substrate comprimising approximately 96% $Al_2O_3$ and approximately 4% binder, available from Coors Ceramic Company, Grand Junction, Colorado. The laser score process needed for wafer singulation is available from Lasereliance Technologies, Altamonte Springs, Fla. Using the thick-film deposition technique, a conductive strip was fabricated by screen printing, using a framed, stainless 325 mesh/0.01 mm emulsion-coated screen available from Affiliated Manufacturers, Inc., North Branch, N.J. The silver conductive paste printed is available, Part No. 3571 UF, from Metech Company of Elverson, Pa. The conductive strip was fabricated so as to create an oval electrode with the approximate dimensions of 1.52 mm×0.762 mm. The paste was fired using a Fast Fire, 7 zone belt furnace with an attached 3 zone dryer available from BTU of Billerica, Mass., in accordance with manufacturer's recommendations. Subsequently, a gold conductor and contact pad was screen printed so as to overlap and make contact to the silver conductor. The contact pad extends approximately 2.03 mm from the Dielectric coating edge and has a contact area of approximately 1.66 mm. The gold paste is available as part no. MTPC10391 from Metech Company, Elverson, Pa. Firing was carried out according to manufacturer's recommendations. A dielectric (glass) passivation was then printed over both conductors with openings so as to define the active electrode area and the contact pads. The dielectric paste, part no. 9615, is available from E. I. Dupont, Wilmington, Del., and was fired according to manufacturer's recommendations.

The gold contact pads were masked with 0.250" skived TFE film tape with a silicon adhesive available from Green Rubber, Cambridge, Mass. The silver electrodes were then galvanostatically plated with silver chloride from 0.1M KCL for 10 minutes at −2.00 mA. The tape was removed and the chip was rinsed in deionized water and air dried.

EXAMPLE 2

A copolymer of MAPTAC and MMA was synthesized according to the following method. MAPTAC was purchased as a 50 weight percent aqueous solution inhibited with 600 ppm MEHQ from Aldrich of Milwaukee, Wis., and was used as received. MMA was purchased from Aldrich of Milwaukee, Wis., and was distilled prior to use. Isopropyl alcohol (IPA) was HPLC grade from Fisher of Pittsburgh, Pa., and was used as received. Anhydrous ethanol was from Quantum Chemical of Cincinnati, Ohio, and was used as received. Azobisisobutyronitrile (AIBN) was from Kodak Chemical of Rochester, N.Y., and was recrystallized in acetone prior to use. Anhydrous diethyl ether was from Fisher, and was used as received. A copolymer having a weight ratio of 25 parts MAPTAC to 75 parts MMA was synthesized as follows. 10 mL of IPA, 5 g of a 50 weight percent aqueous solution of MAPTAC and 7.5 g of MMA were added to a test tube which was then covered with a septum. A needle connected to a nitrogen line was inserted into the septum and the reaction mixture was mixed with nitrogen bubbles for about 5 minutes. 0.11 g of AIBN was next added to the reaction mixture and this was mixed for an additional 20 minutes with nitrogen bubbles. The needle was removed and the test tube was placed in a 70° C. water bath for 2.5 hours. The water bath was then removed and the test tube sat capped overnight at room temperature. The polymer was removed from the test tube by breaking the glass. Pieces of polymer were dissolved in a 10% solution of anhydrous ethanol, precipitated into anhydrous diethyl ether, filtered, and then dried 30 minutes with vacuum.

EXAMPLE 3

Silated PVC was synthesized in house, according to commonly-owned, pending U.S. patent application Ser. No. 07/817,721, filed Jan. 7, 1992. A 25/75 weight ratio of MAPTAC/MMA, prepared according to Example 2, was dissolved as a 5% weight solution in ethanol. A chip fabricated according to Example 1 was prepared as described in Example 1, and the ethanol solution containing MAPTAC/MMA was drop cast thereover using a Pasteur pipette. The ethanol was driven off by drying at room temperature followed by drying at 80° C. for 30 minutes. The resultant MAPTAC/MMA layer had a thickness of about 10 $\mu$m. The chip was then spun cast with a 1% weight solution of silated PVC in tetrahydrofuran at 4,000 RPM for 30 seconds and cured for 2 hours at 80° C. The resultant silated PVC layer had a thickness of about 1 $\mu$m.

EXAMPLE 4

A chip including a membrane selective for hydrogen ion (a pH sensor) was fabricated as follows. The pH sensor was prepared by depositing a hydrogen ion selective membrane atop the sensor fabricated in accordance with Example 3 according to the following method. Tetrahydrofuran (THF) was purchased from Aldrich, of Milwaukee, Wis. Tridodecylamine (TDDA) was purchased from Fluka, of Buchs, Switzerland. Potassium tetrakis (p-chlorophenyl) borate (KTpClPB) was purchased from Fluka. Dioctylphthalate (DOP) was purchased from Fluka. PVC was purchased from Fluka. A 10% by weight membrane solution was prepared in THF containing 2 weight percent TDDA, 0.1 weight percent KTpClPB, 65 weight percent DOP, and 33 weight percent PVC. A volume of 3.6 ml of membrane solution was solvent cast onto a chip fabricated in accordance with Example 3. The layer was dried at room temperature in a THF environment for about 24 hours. Final membrane thickness was approximately 120 $\mu$m.

EXAMPLE 5

A chip including a membrane selective for the potassium ion was fabricated as follows. Valinomycin (VAL) was purchased from Fluka. Diundecylphthalate (DUP) was, purchased from Scientific Polymer Products of Ontario, N.Y. A 10% by weight membrane solution was formulated in THF containing 1 weight percent VAL, 33 weight percent PVC, 66 weight percent DUP, and 0.2 weight percent KTpClPB. A membrane layer was cast atop a chip fabricated in accordance with Example 1 as described in Example 4.

EXAMPLE 6

A chip including a membrane selective for the sodium ion was fabricated as follows. Methyl monensin ester (MMO) was purchased from Calbiochem of LaJolla, Calif. o-nitrophenol octyl ether (NPOE) was purchased from Fluka.

A 10% by weight membrane solution was formulated in THF containing 2 weight percent MMO, 30 weight percent PVC, 67.6 weight percent o-NPOE, and 0.4 weight percent KTpClPB. A membrane layer was cast atop a chip fabricated in accordance with Example 3 in the manner described in Example 4.

EXAMPLE 7

A chip including a membrane selective for the calcium ion was fabricated as follows: (R,R)-N,N'-[BIS(11-ethoxycarbonyl)undecyl]-NN'-4,5-tetramethyl-3,6-doxaoctane diamide (ETH1001) was purchased from Fluka. A 10 percent by weight solution in THF was prepared by adding 3.3 weight percent ETH1001, 1.2 weight percent KTpClPB, 30 weight percent PVC, and 6.5.5 weight percent NPOE. The solution was solvent cast onto a chip prepared in accordance with Example 3 in the manner described in Example 4.

EXAMPLE 8

Five day whole blood and serum studies were conducted for pH sensors using chips fabricated in accordance with Example 4. Sample chambers were constructed so as to expose all sample solutions to an area of the ion selective membrane immediately above the reference redox couple. A conventional silver/silver chloride reference electrode and the gold contact pad of the pH chip were connected to a high impedance voltmeter, the reference electrode also being exposed to sample solutions.

Seven sensors were tested. The sensors were first wetup in pH 7 buffer and initial slopes were determined. The sensors were then soaked for approximately 48 hours in the buffer solution.

On day one, potentiometric selectivity coefficients were determined using the fixed interference method. Buffer solutions were: 1) 10 mM NaOH, 130 mM NaCl, 10 mM TRIS, 2) 190 mM KCl, 10 mM KOH, 10 mM TRIS, 3) 60 mM LiOH, 6.6 mM citric acid, 11.4 mM boric acid, 4) 130 mM $CaCl_2$, 20 mM $Ca(OH)_2$, 10 mM TRIS, and 5) 130 mM $MgCl_2$, 20 mM $Mg(OH)_2$, 10 mM TRIS. The pH of each solution was adjusted by dropwise addition of 1N HCl. Slope was determined at the end of the day.

On days 2–4, the following test sequence was carried out: (A) aqueous test (slope determination and triplicate measurements of a variety of pH standard solutions); (B) the pH of 20 samples of human serum was measured; (C) aqueous test, as in (A); (D) pH measurement of 10 human whole blood samples, followed by a slope determination (WB 1); (E) a repeat of step (D) for a second blood sample (WB 2); (F) a repeat of step (D) for. a third blood sample (WB 3); (G) a repeat of the aqueous test of step (A).

The results of this test are given in Table 1. The average readings of each of the seven sensors are displayed along with standard deviation and % cv, measured against the results of a control pH test run on the same samples using a commercially available pH sensor (Ciba Corning Diagnostics Corp., 200 series glass pH electrode). The results show good precision and accuracy of pH measurement carried out in accordance with the ion selective pH sensor of the present invention. Selectivity of the pH sensor of the present invention, with respect to lithium, sodium, potassium, magnesium, and calcium were determined using the fixed interference method. Selectivity, slope, and linearity of the sensor was good.

EXAMPLE 9

The five (5) day whole blood and serum study of Example 8 was carried out using potassium sensors using chips fabricated in accordance with Example 5. Four potassium sensors were fabricated. On day 1, potentiometric selectivity coefficients were determined using the separate solution method. Results were similar to conventional $K^+$ electrodes. On days 2–4, the test sequence described in Example 8 was carried out, with the exception that step A was carried out using 644 Cal and 644 Slope solutions, commercially available from Ciba Corning Diagnostics of Medfield, Mass. and potassium was measured rather than pH. The results of this test are given in Tables 2 and 3. The average readings of each of the four sensors are displayed along with standard deviation and % CV, measured against the results of a control potassium test run on the same samples using a commercially available potassium sensor (Ciba Corning Diagnostics Corp. 200 series potassium electrode). The accuracy and precision of the blood and serum feasibility test was very good. Slope, linearity, and selectivity coefficients were also good.

EXAMPLE 10

The five day whole blood and serum study described in Example 8 was conducted for sodium sensors using chips fabricated in accordance with Example 6. Sample chambers were constructed as in Example 8. The slope and calibration solutions described in Example 9 were used. The control sensor was a commercially available sodium sensor (Ciba Corning Diagnostics Corp. 200 series glass sodium sensor). Table 4 gives average precision values for 5 sensors fabricated according to this example. The results are very good. Slope, linearity, and selectivity were also good.

EXAMPLE 11

The five day whole blood and serum study described in Example 8 was conducted for calcium sensors including chips fabricated in accordance with Example 7. Five sensors were fabricated. Sample chambers were constructed in accordance with Example 8. The slope and calibration solutions were 634 cal and 634 slope solutions, commercially available from Ciba Corning Diagnostics Corp. Table 5 lists average precision values. Precision and accuracy are very good. Linearity, slope and selectivity were also good.

EXAMPLE 12

Transference number determinations in the MAPTAC/MMA membrane material fabricated in accordance with Example 2, were carried out. Free-standing MAPTAC/MMA was formed by drop casting from a 5 weight percent solution in ethanol, similar to the drop casting method described in Example 3. The free-standing membranes, after air-drying, had a thickness of approximately 82 $\mu$m. The membranes were soaked in 160 mM solution of NaCl for about 30 minutes, and swelled to about 2.1 times their dry weight as a result. Circular sections were cut out of the free-standing membranes and mounted in the well-known Phillips bodies. The fill solution was the same as the soak solution and a silver/silver chloride internal reference was used. EMF measurements were made in beakers with a saturated KCl calomel reference electrode. Transference numbers were determined by the EMF method whereby membrane potentials are measured using electrolyte concentrations C1 and C2 on either side of the membrane. The concentration of NaCl on one side was kept constant at 160 mM and the concentration C2 of NaCl or $KNO_3$ on the other side was varied. Reference to this well-known method may be found in "Transport Phenomena in Membranes", by N. Lakshminarayanaiah, N.Y., Academic Press, (1969). Results are tabulated in Table 6. Appreciable cationic as well as anionic transport in the films tested was observed. Ionic transport was also observed to be a non-selective phenomenon, as evidenced by the similarity in the results when NaCl is replaced by $KNO_3$.

EXAMPLE 13

A pH sensor was prepared in accordance with Example 4. A 25/75 weight ratio of MAPTAC/MMA in ethanol was spun cast on the chip for 30 seconds at 750 RPM. The chip was air dried. A pH membrane was cast atop the chip in accordance with Example 4. Using 6200C Permanent Mending Tape from 3M Corporation of St. Paul, Minn., the tape was pressed atop the chip and slowly removed by pulling upwards at an angle approximately perpendicular to the surface of the chip. Adhesion was observed to be good. Aqueous performance was tested over 40 days and was very good.

EXAMPLE 14

An ion selective sensor is fabricated as in Example 1 except that the membrane includes 96.7% EVA(45), 3% valinomycin and 0.3% $KB(C_6H_4Cl)_4$ by weight and is prepared as follows. 6.5 ml of EVA (45) (Item number 784 Scientific Polymer Products, Ontario, N.Y. 14519, molecular weight of 260,000 as measured by gel permeation chromatography, melt index of 2–5 measured according to ASTM D 1238-62 T, softening point of 182° C.) dissolved in distilled tetrahydrofuran (THF) (Aldrich Chemical Co. located in Milwaukee, Wiss.) to a concentration of 30 mg/ml is mixed with 3 ml of valinomycin (Sigma, St. Louis, Mo.) and is dissolved in THF to a concentration of 2 mg/ml. 0.6 ml of $KB(C_6H_4Cl)_4$ (Fluka of Buchs, Switzerland) dissolved in THF to a concentration of 1 mg/ml is added to the EVA (45)/valinomycin solution. This EVA/45 valinomycin/KB $(C_6H_4Cl)_4$ solution is mixed with a magnetic stir bar for one hour at room temperature under atmospheric pressure then is prepared as in Example 1. It is believed that the membrane has a crystallinity below approximately 3%.

EXAMPLE 15

An ion selective sensor is fabricated as in Example 14 except that ETH1001 (Molecular formula $C_{38}H_{72}N_2O_8$, molecular weight 685.01, selectophore grade, Fluka of Buchs, Switzerland) is replaced for valinomycin. It is believed that the crystallinity of the membrane is below approximately 3%.

EXAMPLE 16

An ion selective sensor is fabricated as in Example 14 except that nonactin (Sigma located in St. Louis, Mo.) is substituted for valinomycin. It is believed that the crystallinity of the membrane is below approximately 3%.

EXAMPLE 17

An ion selective sensor is fabricated as in Example 1 except that the membrane comprises 29% PVC (Fluka of Buchs, Switzerland) 49.1% EVA (45), 20% dioctyl adipate (DOA) (selectophore grade Fluka of Buchs, Switzerland), 1% valinomycin and 0.1% KB $(C_6H_4Cl)_4$ (Fluka of Buchs, Switzerland) by weight and is prepared as follows. 3.25 ml of EVA (45) having a concentration of 30 mg/ml is mixed with 1 ml of a valinomycin solution having a concentration of 2 mg/ml. 0.2 ml of $KB(C_6H_4Cl)_4$ having a concentration of 1 mg/ml is added to the solution. Finally 39 mg of DOA and 56.5 mg of PVC, previously dissolved in 3 ml of distilled THF, is added to this solution, and the membrane is then prepared as in Example 1. It is believed that the crystallinity of the membrane is below approximately 3%.

The preceding examples are set forth to illustrate specific embodiments of the invention and are not intended to limit the scope of the invention. Additional embodiments and advantages within the scope of the claimed invention, for example measuring electoactive species other than simple inorganic ions, will be apparent to those of ordinary skill in the art.

TABLE 1

| | | | pH: WHOLE BLOOD AND SERUM SENSOR NO. | | | | | | | |
|---|---|---|---|---|---|---|---|---|---|---|
| | | | 1 | 2 | 3 | 4 | 5 | 6 | 7 | CONTROL |
| Day 2 | serum | avg | 8.061587 | 8.055022 | 8.072486 | 8.079076 | 8.098774 | 8.071817 | 8.057097 | 8.005298 |
| | | SD | 0.012465 | 0.010118 | 0.014113 | 0.015777 | 0.013251 | 0.015623 | 0.013466 | 0.011889 |
| | | % cv | 0.154619 | 0.125592 | 0.174827 | 0.195283 | 0.193556 | 0.163619 | 0.167135 | 0.148515 |
| | WB 1 | avg | 7.706525 | 7.695725 | 7.701741 | 7.68968 | 7.693139 | 7.698948 | 7.694457 | 7.603658 |
| | | SD | 0.009755 | 0.007797 | 0.008811 | 0.019299 | 0.016945 | 0.018739 | 0.015882 | 0.016429 |
| | | % cv | 0.126575 | 0.101321 | 0.114402 | 0.250968 | 0.220263 | 0.243398 | 0.206411 | 0.216065 |
| | WB 2 | avg | 7.699835 | 7.684835 | 7.692228 | 7.684354 | 7.68996 | 7.694301 | 7.688545 | 7.574038 |
| | | SD | 0.00237 | 0.002147 | 0.001877 | 0.002363 | 0.003676 | 0.002652 | 0.002929 | 0.002591 |
| | | % cv | 0.030786 | 0.027932 | 0.024396 | 0.030755 | 0.047802 | 0.034466 | 0.03809 | 0.034212 |
| | WB 3 | avg | 7.705122 | 7.688145 | 7.696397 | 7.688071 | 7.696104 | 7.698188 | 7.693823 | 7.5846 |
| | | SD | 0.001594 | 0.001889 | 0.001267 | 0.001848 | 0.002384 | 0.001474 | 0.002554 | 0.002283 |
| | | % cv | 0.020687 | 0.0245572 | 0.016461 | 0.024042 | 0.030972 | 0.019111 | 0.033201 | 0.030099 |
| Day 3 | serum | avg | 8.049192 | 8.040586 | 8.043998 | 8.05155 | 8.054434 | 8.051513 | 8.042659 | 7.989721 |
| | | SD | 0.01013 | 0.00927 | 0.009733 | 0.009183 | 0.012032 | 0.011378 | 0.011184 | 0.009878 |
| | | % cv | 0.125846 | 0.115294 | 0.121002 | 0.11407 | 0.149383 | 0.141316 | 0.139062 | 0.123637 |
| | WB 1 | avg | 7.671816 | 7.64788 | 7.666324 | 7.661085 | 7.67144 | 7.66472 | 7.665776 | 7.566504 |
| | | SD | 0.015767 | 0.012876 | 0.012965 | 0.014039 | 0.019848 | 0.018604 | 0.017862 | 0.00688 |
| | | % cv | 0.205513 | 0.16836 | 0.16911 | 0.183256 | 0.258727 | 0.242718 | 0.233013 | 0.090932 |
| | WB 2 | avg | 7.710719 | 7.684293 | 7.704729 | 7.700617 | 7.710989 | 7.699919 | 7.698856 | 7.589368 |
| | | SD | 0.009972 | 0.007915 | 0.009009 | 0.010334 | 0.014195 | 0.011513 | 0.011141 | 0.007044 |
| | | % cv | 0.129324 | 0.103 | 0.116927 | 0.134196 | 0.184085 | 0.149524 | 0.144712 | 0.092816 |
| | WB 3 | avg | 7.725511 | 7.701296 | 7.721992 | 7.714652 | 7.724535 | 7.714606 | 7.714507 | 7.603402 |
| | | SD | 0.006266 | 0.00385 | 0.005618 | 0.006141 | 0.008245 | 0.006667 | 0.00799 | 0.007351 |
| | | % cv | 0.081109 | 0.049998 | 0.072753 | 0.079605 | 0.106733 | 0.086421 | 0.103568 | 0.096676 |
| Day 4 | serum | avg | 8.054572 | 8.05256 | 8.056934 | 8.062627 | 8.068998 | 8.101428 | 8.056291 | 8.000674 |
| | | SD | 0.009893 | 0.008643 | 0.009516 | 0.010136 | 0.01189 | 0.016209 | 0.010325 | 0.010781 |
| | | % cv | 0.12282 | 0.107328 | 0.138104 | 0.125717 | 0.147359 | 0.200076 | 0.128158 | 0.134749 |
| | WB 1 | avg | 7.653196 | 7.629177 | 7.65007 | 7.646547 | 7.653276 | 7.667271 | 7.648862 | 7.547893 |
| | | SD | 0.011171 | 0.006606 | 0.00967 | 0.009947 | 0.012524 | 0.013148 | 0.009121 | 0.002723 |
| | | % cv | 0.145962 | 0.086595 | 0.126408 | 0.130086 | 0.163642 | 0.171479 | 0.119242 | 0.036075 |

TABLE 1-continued pH: WHOLE BLOOD AND SERUM

| | | SENSOR NO. | | | | | | | |
|---|---|---|---|---|---|---|---|---|---|
| | | 1 | 2 | 3 | 4 | 5 | 6 | 7 | CONTROL |
| WB 2 | avg | 7.656357 | 7.623297 | 7.645822 | 7.64422 | 7.655154 | 7.700881 | 7.649585 | 7.508605 |
| | SD | 0.011384 | 0.008108 | 0.007122 | 0.010447 | 0.013335 | 0.011147 | 0.013093 | 0.002409 |
| | % cv | 0.148684 | 0.106358 | 0.093153 | 0.13666 | 0.174192 | 0.144755 | 0.171163 | 0.032079 |
| WB 3 | avg | 7.726021 | 7.691833 | 7.715495 | 7.714141 | 7.711244 | 7.772353 | 7.712899 | 7.584241 |
| | SD | 0.011128 | 0.008903 | 0.011885 | 0.011111 | 0.019226 | 0.014096 | 0.013054 | 0.008243 |
| | %cv | 0.144038 | 0.115751 | 0.154041 | 0.144034 | 0.249318 | 0.181362 | 0.169251 | 0.108689 |
| | avg | 7.670686 | 7.655651 | 7.667248 | 7.663609 | 7.667841 | 7.666509 | 7.659115 | 7.584853 |
| | SD | 0.011073 | 0.008864 | 0.011907 | 0.011031 | 0.01978 | 0.013553 | 0.013017 | 0.008274 |
| | % cv | 0.144355 | 0.115789 | 0.155293 | 0.143942 | 0.257959 | 0.176779 | 0.169954 | 0.109082 |

TABLE 2

K+, SERUM

| | SERUM mM CONCENTRATION | | | PRECISION % CV | | |
|---|---|---|---|---|---|---|
| SENSOR # | DAY 2 | DAY 3 | DAY 4 | DAY 2 | DAY 3 | DAY 4 |
| 1 | 4.45 | 4.34 | 4.29 | 1.80 | 0.22 | 0.27 |
| 2 | 4.58 | 4.33 | 4.34 | 0.83 | 0.26 | 0.30 |
| 3 | 4.58 | 4.36 | 4.31 | 0.97 | 0.20 | 0.18 |
| 4 | 4.43 | 4.35 | 4.34 | 0.87 | 0.14 | 0.10 |
| CONTROL | 4.38 | 4.33 | 4.33 | 0.52 | 0.40 | 0.34 |

TABLE 3

K+, WHOLE BLOOD

| | SENSOR NO. | | | | |
|---|---|---|---|---|---|
| | 1 | 2 | 3 | 4 | CONTROL |
| DAY 2 | 4.40 | 4.34 | 4.36 | 4.34 | 4.33 |
| | 0.03 | 0.04 | 0.03 | 0.03 | 0.01 |
| | 0.77 | 0.81 | 0.80 | 0.68 | 0.28 |
| | 4.29 | 4.20 | 4.23 | 4.21 | 4.23 |
| | 0.03 | 0.04 | 0.03 | 0.03 | 0.02 |
| | 0.69 | 0.85 | 0.62 | 0.62 | 0.46 |
| | 4.24 | 4.17 | 4.20 | 4.21 | 4.16 |
| | 0.02 | 0.02 | 0.03 | 0.02 | 0.02 |
| | 0.53 | 0.47 | 0.61 | 0.46 | 0.42 |
| DAY 3 | 4.15 | 4.04 | 4.09 | 4.10 | 4.01 |
| | 0.03 | 0.04 | 0.04 | 0.04 | 0.01 |
| | 0.74 | 1.00 | 0.94 | 0.88 | 0.31 |
| | 4.15 | 4.06 | 4.12 | 4.10 | 4.11 |
| | 0.03 | 0.03 | 0.03 | 0.03 | 0.02 |
| | 0.67 | 0.69 | 0.68 | 0.67 | 0.45 |
| | 3.72 | 3.65 | 3.68 | 3.68 | 3.57 |
| | 0.03 | 0.03 | 0.03 | 0.03 | 0.01 |
| | 0.70 | 0.85 | 0.81 | 0.87 | 0.26 |
| DAY 4 | 4.18 | 4.11 | 4.26 | 4.16 | 4.12 |
| | 0.05 | 0.04 | 0.06 | 0.04 | 0.00 |
| | 1.11 | 1.08 | 1.39 | 0.96 | 0.08 |
| | 4.03 | 4.01 | 4.00 | 4.03 | 4.00 |
| | 0.03 | 0.03 | 0.08 | 0.03 | 0.00 |
| | 0.65 | 0.65 | 1.88 | 0.75 | 0.10 |
| | 3.82 | 3.79 | 3.83 | 3.80 | 3.81 |
| | 0.03 | 0.02 | 0.03 | 0.02 | 0.01 |
| | 0.76 | 0.60 | 0.77 | 0.61 | 0.38 |

TABLE 4

Na+ SENSOR PRECISION

| WHOLE BLOOD | | SERUM | |
|---|---|---|---|
| +/− | 1.4% | +/− | 0.45% |
| | 1.6 | | 0.40 |
| | 1.3 | | 0.95 |
| | 1.1 | | 0.58 |
| | 1.5 | | 0.38 |

TABLE 5

Ca++ SENSOR PRECISION

| WHOLE BLOOD | | SERUM | |
|---|---|---|---|
| +/− | 1.6% | +/− | 1.6% |
| | 1.7 | | 2.1 |
| | 1.9 | | 0.8 |
| | 1.9 | | 2.3 |
| | 2.7 | | 1.3 |

TABLE 6

TRANSFERENCE NUMBER MEASUREMENTS

| $C_2$ range | slope | $r^2$ | $t_+$ | $t_-$ |
|---|---|---|---|---|
| 0.12–0.20M NaCl | 41.9 | 0.984 | 0.35 | 0.65 |
| 0.12–0.20M KNO$_3$ | 27.0 | 0.940 | 0.23 | 0.77 |
| $10^{-5}$–1M NaCl | 33.5 | 0.983 | 0.28 | 0.72 | slope = Slope of Cell EMF
$r^2$ = Correlation Coefficient
$t_+$ = Cation Transference Number
$t_-$ = Anion Transference Number

What is claimed is:

1. An ion selective solid state sensor, comprising:
an electrically conductive material providing a reference redox couple, said electrically conductive material including mobile ions having a first charge;
an acrylic polymeric material having immobilized ions and being in direct contact with said electrically conductive material, said immobilized ions having a second charge opposite said first charge, said acrylic polymeric material being provided on said electrically conductive material; and
an ion selective membrane covering said polymeric material, said ion selective membrane comprising an ethylene vinyl acetate polymer, said ethylene vinyl acetate polymer including from about 30 weight percent to about 75 weight percent vinyl acetate monomer and from about 0 percent to about 20 percent by weight plasticizer, and an ion selective material dispersed within said ethylene vinyl acetate polymer, wherein said ion selective membrane is from about 0 percent crystalline to about 10 percent crystalline, and wherein said ion selective membrane is not in direct physical contact with said electrically conductive material but is in contact with said acrylic polymeric material.

2. An ion selective sensor in accordance with claim 1, wherein said ethylene vinyl acetate polymer includes from about 35 weight percent to about 55 weight percent vinyl acetate monomer and from about 0 percent to about 5 percent by weight plasticizer.

3. An ion selective sensor in accordance with claim 2, wherein said ethylene vinyl acetate polymer is substantially devoid of plasticizer.

4. An ion selective sensor in accordance with claims 1, 2 or 3, wherein said ethylene vinyl acetate polymer includes from about 40 weight percent to about 50 weight percent vinyl acetate monomer.

5. An ion selective sensor in accordance with claims 1, 2 or 3, wherein said ethylene vinyl acetate polymer includes about 45 weight percent vinyl acetate monomer.

6. An ion selective sensor in accordance with claim 2, wherein said membrane comprises from about 0.1 percent to about 10 percent of said ion selective material by weight.

7. An ion selective sensor in accordance with claim 6, wherein said membrane comprises from about 1 percent to about 6 percent of said ion selective material by weight.

8. An ion selective sensor in accordance with claims 1, 2 or 3, wherein said ion selective membrane further comprises a salt uniformly incorporated in said membrane, said salt having a mole percent of said membrane so as to permit increased ion transport within said membrane.

9. An ion selective sensor in accordance with claim 8, wherein said mole percent of said salt is from about 10 percent to about 80 percent of said mole percent of said ion selective material.

10. An ion selective sensor in accordance with claim 8, wherein said mole percent of said salt is from about 33 percent to about 66 percent of said mole percent of said ion selective material.

11. An ion selective sensor in accordance with claims 1, 2 or 3, wherein said membrane has a slope of at least about 50 millivolts per decade of analyte concentration.

12. An ion selective sensor in accordance with claims 1, 2 or 3, wherein said membrane has a slope of at least about 55 millivolts per decade of analyte concentration.

13. An ion selective sensor in accordance with claims 1, 2 or 3, wherein said membrane is from about 0% crystalline to about 5% crystalline.

14. An ion selective sensor in accordance with claims 1, 2 or 3, wherein said membrane is from about 0% crystalline to about 3% crystalline.

15. An ion selective sensor in accordance with claim 1, further comprising:

polyvinyl chloride polymer combined with said ethylene vinyl acetate polymer, wherein said membrane comprises from about 0.1 percent to about 50 percent by weight of said polyvinyl chloride polymer.

16. A chemical responsive solid state field effect transducer, comprising:

a layer of semiconductor material having a surface;

a pair of first diffusion regions of a first doping characteristic at said surface, a region of said surface of said layer of semiconductor material existing between said pair of first diffusion regions;

a second diffusion region of a second doping characteristic at said region of said surface of said layer of semiconductive material existing between said pair of first diffusion regions;

an electrically insulating material provided at said region of said surface of said layer of semiconductor material existing between said pair of first diffusion regions;

an acrylic polymeric material in direct contact with said diffusion regions and, having immobilized charged sites provided on said electrically insulating material, said acrylic polymeric material carrying less than about $1.63 \times 10^{21}$ immobilized charged sites per gram, said acrylic polymeric material separated from said diffusion regions by said insulating material;

an ion selective membrane provided in direct contact on said acrylic polymeric material, said ion selective membrane comprising an ethylene vinyl acetate polymer including from about 30 weight percent to about 75 weight percent vinyl acetate monomer and from about 0 percent to about 20 percent by weight plasticizer, and an ion selective material dispersed within said ethylene vinyl acetate polymer, wherein said ion selective membrane is from about 0 percent crystalline to about 10 percent crystalline; and an electrically insulating encapsulant sealing said transducer at a sample region while leaving exposed a region of said ion selective membrane for exposure to a sample, wherein said acrylic polymeric material in not in direct physical contact with said sample.

17. An transducer in accordance with claim 16, wherein said ethylene vinyl acetate polymer includes from about 35 weight percent to about 55 weight percent vinyl acetate monomer and from about 0 percent to about 5 percent by weight plasticizer.

18. A transducer in accordance with claim 17, wherein said ethylene vinyl acetate polymer is substantially devoid of plasticizer.

19. A transducer in accordance with claim 16, wherein said ethylene vinyl acetate polymer includes from about 40 weight percent to about 50 weight percent vinyl acetate monomer.

20. A transducer in accordance with claim 16, wherein said ethylene vinyl acetate polymer includes about 45 weight percent vinyl acetate monomer.

21. A transducer in accordance with claim 16, wherein said membrane comprises from about 0.1 percent to about 10 percent of said ion selective material by weight.

22. A transducer in accordance with claim 21, wherein said membrane comprises from about 1 percent to about 6 percent of said ion selective material by weight.

23. A transducer in accordance with claim 16, wherein said membrane further comprises a salt uniformly incorporated in said membrane, said salt having a mole percent of said membrane so as to permit increased ion transport within said membrane.

24. A transducer in accordance with claim 23, wherein said mole percent of said salt is from about 10 percent to about 80 percent of said mole percent of said ion selective material.

25. A transducer in accordance with claim 23, wherein said mole percent of said salt is from about 33 percent to about 66 percent of said mole percent of said ion selective material.

26. A transducer in accordance with claim 16, wherein said membrane has a slope of at least about 50 millivolts per decade of analyte concentration.

27. A transducer in accordance with claim 16, wherein said membrane has a slope of at least about 55 millivolts per decade of analyte concentration.

28. A transducer in accordance with claim 16, wherein said membrane is from about 0% crystalline to about 5% crystalline.

29. A transducer in accordance with claim 16, wherein said membrane is from about 0% crystalline to about 3% crystalline.

30. A transducer in accordance with claim 16, wherein said membrane further comprises polyvinyl chloride polymer combined with said ethylene vinyl acetate polymer, wherein said membrane comprises from about 0.1 percent to about 50 percent by weight said polyvinyl chloride polymer.

* * * * *